(12) United States Patent
Rhyne et al.

(10) Patent No.: US 10,823,739 B2
(45) Date of Patent: Nov. 3, 2020

(54) IMMUNOASSAY STANDARDS AND MEASUREMENT OF TAU USING INTRA-ASSAY CALIBRATION STANDARDS

(71) Applicant: SALADAX BIOMEDICAL, Bethlehem, PA (US)

(72) Inventors: Paul Rhyne, Princeton, NJ (US); Adam J. Simon, Princeton, NJ (US); Flora Berisha, Princeton, NJ (US); Robert John Neely, Princeton, NJ (US); Christopher J. Spedaliere, Princeton, NJ (US); Claudio Mapelli, Princeton, NJ (US)

(73) Assignee: SALADAX BIOMEDICAL, Bethlehem, PA (US)

( * ) Notice: Subject to any disclaimer, the term of this patent is extended or adjusted under 35 U.S.C. 154(b) by 187 days.

(21) Appl. No.: 14/652,584

(22) PCT Filed: Dec. 18, 2013

(86) PCT No.: PCT/US2013/076046
§ 371 (c)(1),
(2) Date: Jun. 16, 2015

(87) PCT Pub. No.: WO2014/100137
PCT Pub. Date: Jun. 26, 2014

(65) Prior Publication Data
US 2016/0033525 A1 Feb. 4, 2016

Related U.S. Application Data

(60) Provisional application No. 61/745,177, filed on Dec. 21, 2012.

(51) Int. Cl.
C07K 14/47 (2006.01)
C07K 19/00 (2006.01)
G01N 33/68 (2006.01)

(52) U.S. Cl.
CPC ...... *G01N 33/6827* (2013.01); *C07K 14/4711* (2013.01); *G01N 33/6896* (2013.01); *C07K 19/00* (2013.01)

(58) Field of Classification Search
CPC .......... G01N 33/6827; G01N 33/6896; G01N 33/531; G01N 2333/4709; C07K 14/4711; C07K 19/00; A61K 47/10; A61K 47/34; A61K 9/2031
See application file for complete search history.

(56) References Cited

U.S. PATENT DOCUMENTS

2014/0302532 A1* 10/2014 Wilson .............. G01N 33/6896
435/7.92

FOREIGN PATENT DOCUMENTS

| WO | WO 2010091294 A2 * | 8/2010 | ............. A01N 37/46 |
|----|---------------------|--------|-------------------------|
| WO | WO 2011100292 A1 * | 8/2011 | ........... G01N 33/531 |
| WO | WO 2011109112 A2 * | 9/2011 | ......... G01N 33/6896 |

OTHER PUBLICATIONS

Porzig R et al. Epitope mapping of mAbs AT8 and Tau5 directed against hyperphosphorylated regions of the human tau protein. Biochem. Biophys. Res. Comm. 2007, 358:644-649.*
Vanmechelen E et al. Quantification of tau phosphorylated at threonin 181 in human cerebrospinal fluid: a sandwich ELISA with a synthetic phosphopeptide for standardization. Neurosci. Lett. 2000, 285:49-52.*

* cited by examiner

Primary Examiner — Kimberly Ballard

(57) ABSTRACT

The present invention provides novel peptides, compositions, and methods for creating quantitative novel compositions, as well as methods for creating quantitative standards to calibrate analytes. These peptides, compositions, and methods enable the creation of standards and calibrators for analyzing analytes and measuring clinical biomarkers (e.g., Tau). Also provided are kits comprising the peptides or compositions described herein, for use in assays (e.g., sandwich immunoassays).

9 Claims, 9 Drawing Sheets
Specification includes a Sequence Listing.

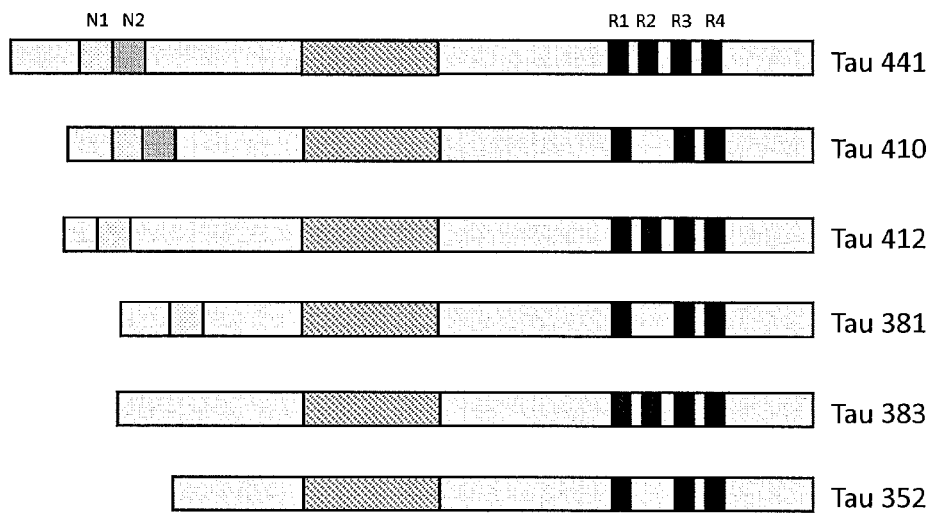
Figure 1: The six isoforms of tau are formed through RNA splicing. There are two possible N-terminal inserts (N1 and N2, gray bars) and four possible C-terminal repeats (R1–R4, black bars). The epitopes used in this invention are from the domain represented in this figure by the bar with the diagonal lines. This domain ranges from amino acid residue 155 to residue 230 of tau 441.

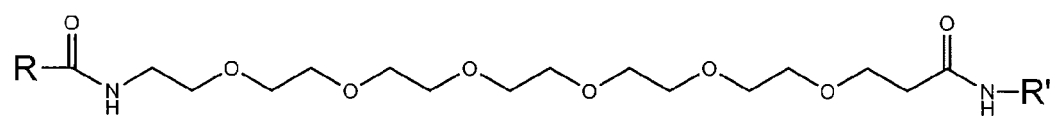
Figure 2: The chemical structure of the (PEG)$_6$ linker. R and R' represent peptides that can be used in this assay.

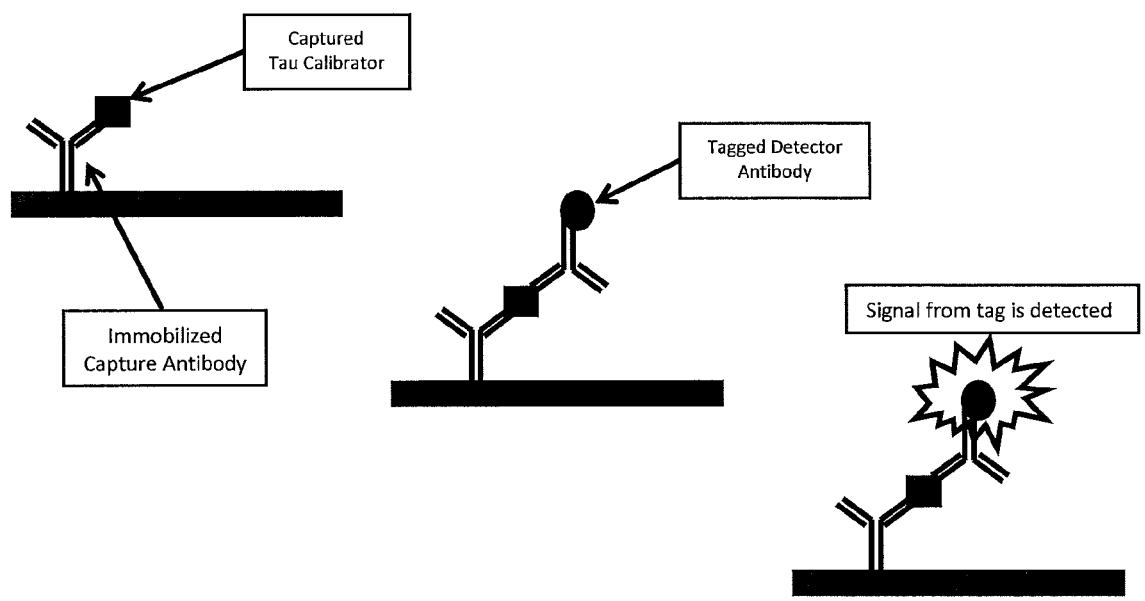
Figure 3: Schematic of a sandwich immunoassay.

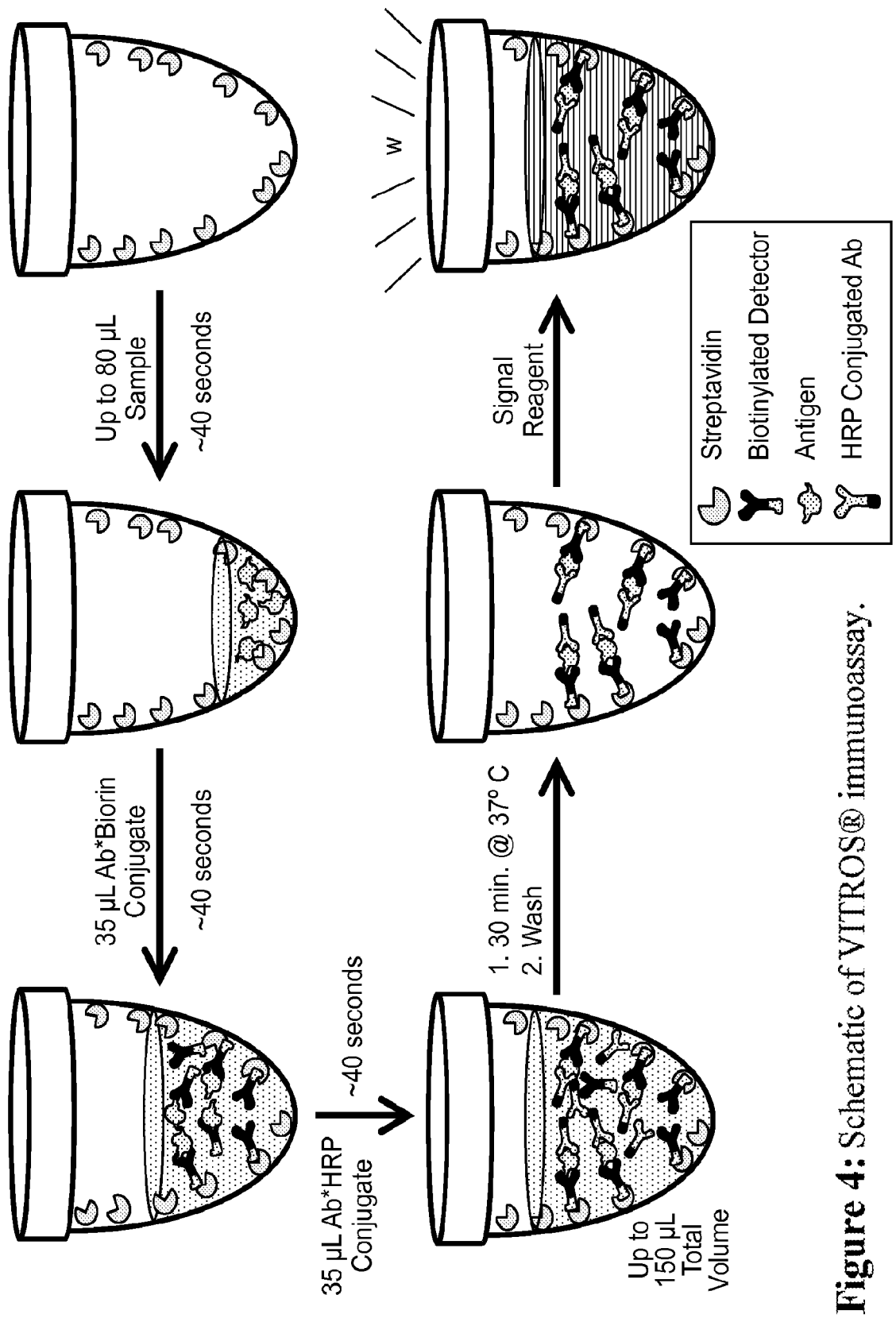
Figure 4: Schematic of VITROS® immunoassay.

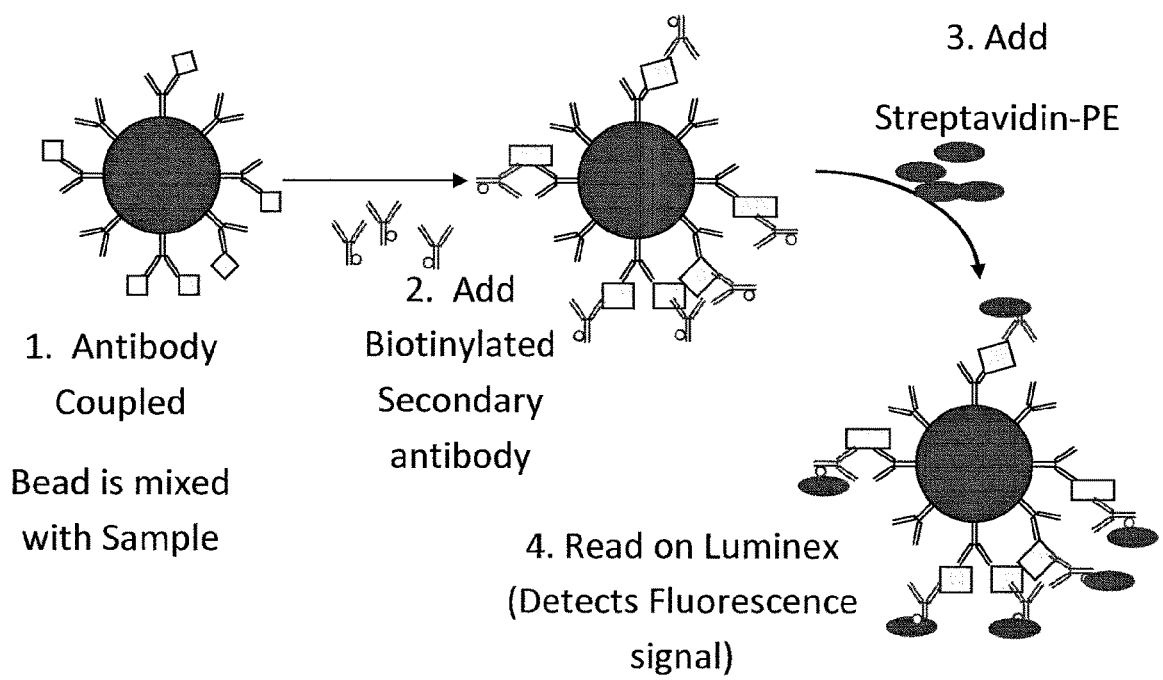
Figure 5: Schematic of Luminex Assay.

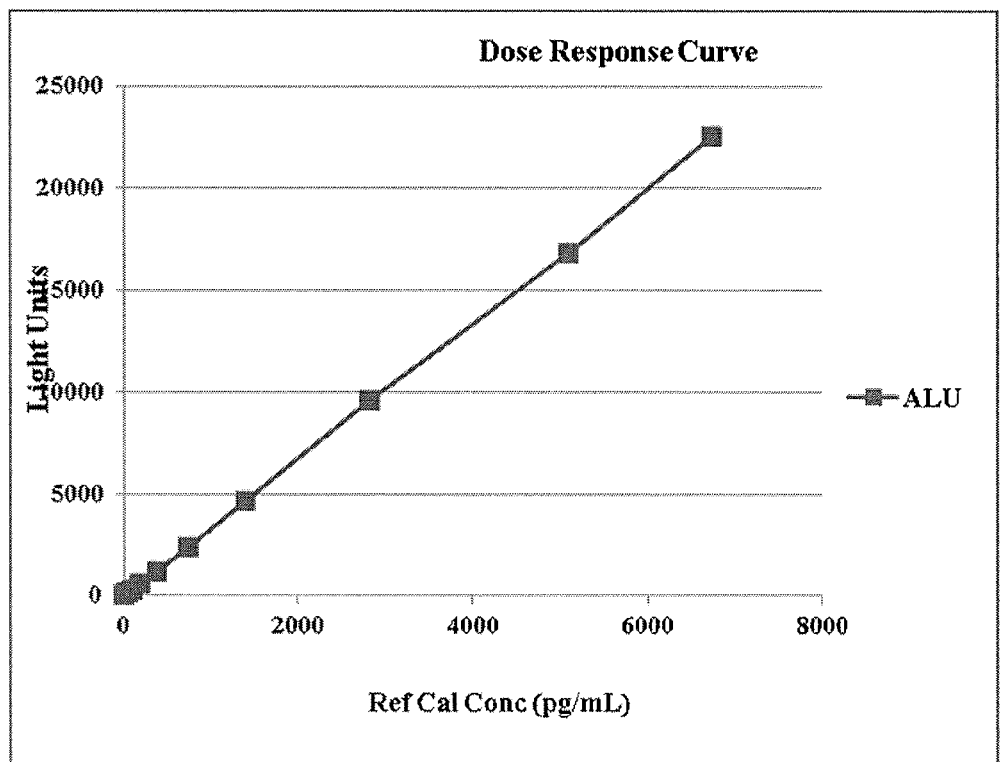
Figure 6: A dose response curve using the modified Tau peptide consisting of native Tau amino acids (190-209)-(PEG)6-native Tau amino acids (215-230) (SEQ ID NO:16) shows that the peptide gives a linear response within the range of the assay.

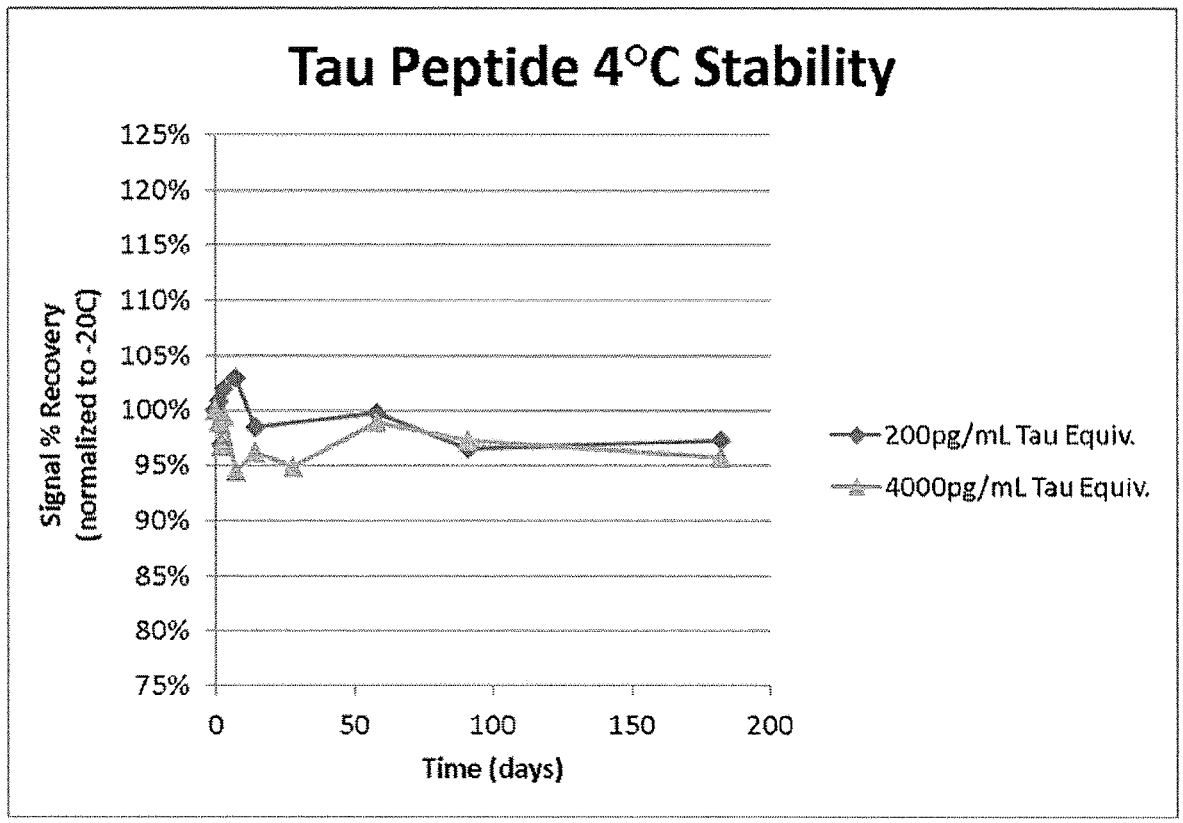
Figure 7: Stability of Tau Peptide consisting of native Tau amino acids (190-209)-(PEG)6-native Tau amino acids (215-230) (SEQ ID NO:16)). This peptide is stable in solution for at least 6 months when stored at 2-8°C. The data for each time point and concentration is normalized to an equivalent sample stored at -20C.

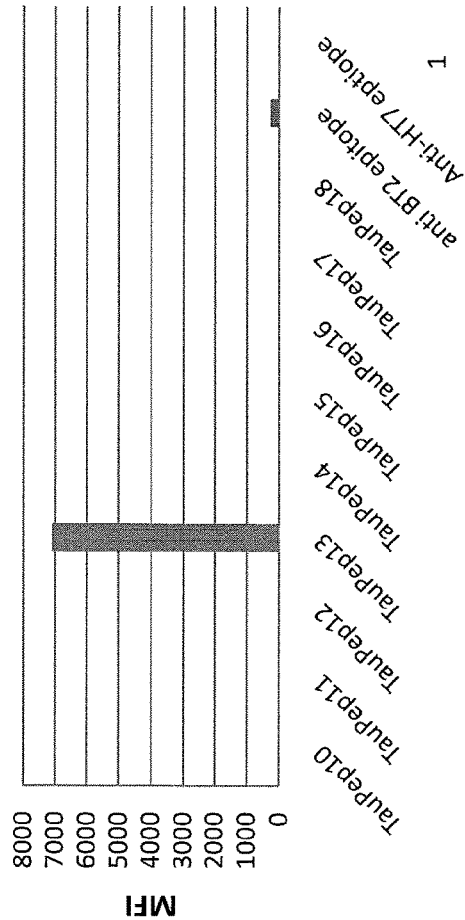

HT7
126-RMVSKSKDGTGSDDKKAKGADGKTKIATPRGAA PGQK QANATRIPAKTPPAPKTPPSS-185
9-KHVTQARMVSKSKDGTGSDDK
10-KGSDDKKAKGADGKTKIATPR
11-KIATPRGAAPPGQKGQANATR
12-KANATRIPAKTPPAPKTPPSS

HT7-peptide CRGAAPPGQKGQANATR

BT2   Tau1                    Tau 5
186-GEPPK SGDRSGYSSPGS GTPGSRSRTPSLPT PPTREPKK VAVV RTPPKPSPSSAKSRLQT-245
13-KTPPSSGEPPKSGDRSGYSSP
14-KGYSSPGSPGTPGSRSRTPSL
15-KRTPSLPTPPTREPKKVAVVR
16-KVAVVRTPPKPSPSSAKSRLQT

BT2-peptide CKSGDRSGYSSPGSPGTPGSR

Tau5-peptide CLPTPPTREPKKVAVVR

Figure 9: Biacore Analysis of 9E9 Antibody

| Peptide | RU<br>25ug/ml (amt of antibody) | RU<br>125ug/ml |
|---|---|---|
| Buffer | 0.1 | |
| Tau 441 (pos control) | 962 | |
| IL23 (neg control) | -0.5 | |
| peptide 15 (8 aa) | -0.2 | |
| peptide 16 | 2.9 | 13.3 |
| peptide 17 | -0.4 | |

US 10,823,739 B2

IMMUNOASSAY STANDARDS AND MEASUREMENT OF TAU USING INTRA-ASSAY CALIBRATION STANDARDS

CROSS-REFERENCE TO RELATED APPLICATIONS

This application is a National Stage Application of PCT/US2013/076046 filed Dec. 18, 2013, which claims priority to and the benefit of U.S. provisional patent application Ser. No. 61/745,177, filed Dec. 21, 2012. The priority of both said PCT and U.S. Provisional Patent Application are claimed. Each of the prior mentioned applications is hereby incorporated by reference herein in its entirety.

SEQUENCE LISTING

The instant application contains a Sequence Listing which has been submitted electronically in ASCII format and is hereby incorporated by reference in its entirety. Said ASCII copy, created on Oct. 8, 2015, is named 105529-86115_SL.txt and is 43,477 bytes in size.

FIELD OF THE INVENTION

The invention relates to peptides and modified peptides that can be used as reference standards and calibrators to measure clinical biomarkers (e.g., Tau) in an immunoassay, as well as methods of measuring the quantity of Tau in a biological sample.

BACKGROUND OF THE INVENTION

Microtubule associated protein Tau (Tau) is a structural protein found in neuronal cells. There are six isoforms of Tau in the human brain resulting from RNA splicing (Himmler, Drechsel et al., 1989). These isoforms differ from one another in having three or four microtubule binding repeats (R) of 31-32 amino acids each in the C-terminal domain, and two, one or none amino terminal inserts (N) of 29 amino acids each (Goedert, Spillantini et al., 1989). Tau can be modified by phosphorylation, glycosylation, and other modifications (Hampel, Blennow et al., 2010). Tau contains repeated C-terminal microtubule binding domains and variable N-terminal domains and differences in the number and type of repeating domains results in the six isoforms (Himmler, Drechsel et al., 1989; Avila, Lucas et al., 2004; Hampel, Blennow et al., 2010). The sequence for the core domain of Tau is identical between the six isoforms and the epitopes used in the design of the present invention are all contained in the core domain, allowing these peptides to represent all six isoforms of Tau (FIG. 1). Tau is an intrinsically disordered protein consisting of random coils with a global hairpin fold (Friedhoff, von Bergen et al., 2000; Jeganathan, von Bergen et al., 2006; Mukrasch, Bibow et al., 2009).

Alzheimer's Disease (AD) is a progressive neurodegenerative disorder that causes dementia. Neurofibrillary tangles (NFT) are found in brain lesions of AD patients and consist of hyperphosphorylated forms of Tau (Hampel, Blennow et al. 2010). Tau exists at elevated levels in the cerebrospinal fluid (CSF) of AD patients and along with phosphorylated Tau (pTau) and $A\beta_{1-42}$, has been shown to be a marker for progression from Mild Cognitive Impairment to Alzheimer's disease (see Avila, Lucas et al., 2004; Mattsson and Zetterberg, 2009; Mattsson, Zetterberg et al., 2009; Hampel, Blennow et al., 2010; and Hampel, Frank et al. 2010).

Tau exists as a heterogeneous mixture in CSF. Multiple isoforms are present and each can be modified by phosphorylation, glycosylation, and digestion (see Goedert, Spillantini et al., 1989; Portelius, Hansson et al., 2008; Hampel, Blennow, et al. 2010; and Hanisch, Soininen et al., 2010). The epitopes used to identify Tau as an AD biomarker in CSF exist in the central domain of Tau that is shared between all six Tau isoforms (see Hampel, Blennow et al., 2010; and Hampel, Frank et al., 2010) (FIG. 1). The core domain of Tau has been shown to exist in CSF as a part of proteolytically cleaved fragments that are extensively modified (see Johnson, Seubert et al., 1997; Portelius, Hansson et al., 2008; and Hanisch, Soininen et al., 2010).

BRIEF SUMMARY OF THE INVENTION

Provided herein are isolated peptides and modified peptides which can be used (e.g., as reference standards) to identify and/or measure levels of Tau in a biological sample.

Representative peptides of the invention include peptides having the amino acid sequence set forth in SEQ ID NO:7, SEQ ID NO:8, SEQ ID NO:9, or SEQ ID NO:10.

Representative modified peptides of the invention include modified peptides which comprise an N-terminal immunoreactive region, a C-terminal immunoreactive region and a linker region, wherein the immunoreactive regions are defined by particular amino acid sequences. In one embodiment, the modified peptide comprises an N-terminal immunoreactive region, a C-terminal immunoreactive region, and a linker region, wherein:
  (a) the N-terminal immunoreactive region comprises or has an amino acid sequence selected from the group consisting of SEQ ID NOs: 7, 8, 9, and 10; and/or
  (b) the C-terminal immunoreactive region comprises or has an amino acid sequence selected from the group consisting of SEQ ID NOs: 7, 8, 9, and 10,
and wherein the N-terminal and C-terminal immunoreactive regions are different amino acid sequences.

In another embodiment, the modified peptide comprises N-terminal and C-terminal immunoreactive regions comprising or having amino acid sequences selected from the group consisting of SEQ ID NOs:7 and 9, SEQ ID NOs:7 and 8, SEQ ID NOs:8 and 9, and SEQ ID NOs:9 and 10, respectively. In another embodiment, the N-terminal and C-terminal immunoreactive regions comprise or have the amino acid sequences set forth in SEQ ID NOs:7 and 9, respectively. In a particular embodiment, the modified peptide is: KSGDRSGYSSPGSPGTPGSR-Generic Linker-LPTPPTREPKKVAVVR (SEQ ID NO: 16). In another embodiment, the modified peptide is: RGAAPPGQK-GQANATR-Generic Linker-KSGDRSGYSSPGSPGT-PGSR (SEQ ID NO:17), RGAAPPGQKGQANATR-Generic Linker-LPTPPTREPKKVAVVR (SEQ ID NO:18), or KTPPSSGEPPKSGDRS-Generic Linker-LPTPPTREPKK-VAVVR (SEQ ID NO:19).

In another embodiment, the modified peptide comprises or has an N-terminal immunoreactive region, a C-terminal immunoreactive region, and a linker region, wherein:
  (a) the N-terminal immunoreactive region comprises or has the amino acid sequence set forth in SEQ ID NO:7 and the C-terminal immunoreactive region comprises or has the amino acid sequence set forth in SEQ ID NO:9

(b) the N-terminal immunoreactive region comprises or has the amino acid sequence set forth in SEQ ID NO:8 and the C-terminal immunoreactive region comprises or has the amino acid sequence set forth in SEQ ID NO:7;

(c) the N-terminal immunoreactive region comprises or has the amino acid sequence set forth in SEQ ID NO:8 and the C-terminal immunoreactive region comprises or has the amino acid sequence set forth in SEQ ID NO:9;

(d) the N-terminal immunoreactive region comprises or has the amino acid sequence set forth in SEQ ID NO:10 and the C-terminal immunoreactive region comprises or has the amino acid sequence set forth in SEQ ID NO:9;

(e) the N-terminal immunoreactive region comprises or has the amino acid sequence set forth in SEQ ID NO:7 and the C-terminal immunoreactive region comprises the amino acid sequence set forth in SEQ ID NO:8;

(f) the N-terminal immunoreactive region comprises or has the amino acid sequence set forth in SEQ ID NO:9 and the C-terminal immunoreactive region comprises or has the amino acid sequence set forth in SEQ ID NO:7;

(g) the N-terminal immunoreactive region comprises or has the amino acid sequence set forth in SEQ ID NO:9 and the C-terminal immunoreactive region comprises the amino acid sequence set forth in SEQ ID NO:8;

(h) the N-terminal immunoreactive region comprises or has the amino acid sequence set forth in SEQ ID NO:12 and the C-terminal immunoreactive region comprises the amino acid sequence set forth in SEQ ID NO:14;

(i) the N-terminal immunoreactive region comprises or has the amino acid sequence set forth in SEQ ID NO:12 and the C-terminal immunoreactive region comprises or has the amino acid sequence set forth in SEQ ID NO:11;

(j) the N-terminal immunoreactive region comprises or has the amino acid sequence set forth in SEQ ID NO:13 and the C-terminal immunoreactive region comprises or has the amino acid sequence set forth in SEQ ID NO:15; or (k) the N-terminal immunoreactive region comprises or has the amino acid sequence set forth in SEQ ID NO:15 and the C-terminal immunoreactive region comprises or has the amino acid sequence set forth in SEQ ID NO:14.

In a particular embodiment, the N-terminal and C-terminal immunoreactive regions comprise or have the amino acid sequences set forth in SEQ ID NOs: 7 and 9, respectively.

Also provided are compositions (e.g., pharmaceutical compositions) comprising the peptides or modified peptides described herein, optionally with a carrier.

Any suitable linker region can be included in the modified peptides described herein. Exemplary linkers include, but are not limited to, polyethylene glycol, a glutamic acid residue, a glycine residue, a serine residue, an alanine residue, a lysine residue, a lipid, a globular protein, a nucleic acid (including but not limited to DNA, RNA, and PNA), and an alkyl chain. In one embodiment, the linker region comprises a PEG6 linker, e.g., having the following structure:

In another embodiment, the linker region comprises or has the amino acid sequence set forth in SEQ ID NO:40 (GGSGGS). In another embodiment, the linker region comprises a non-immunoreactive domain.

Also provided are methods of measuring the quantity of Tau (e.g., Tau 352, Tau 381, Tau 383, Tau 410, Tau 412, or Tau 441) in a biological sample. In one embodiment, the method comprises:

a) attaching a reference standard to at least two beads thereby forming a first bead set and a second bead set, wherein the reference standard comprises an epitope recognized by a first detection antibody and wherein each bead set comprises a different concentration of the reference standard;

b) attaching a capture antibody specific to Tau to a third bead set;

c) combining the bead sets together to form a suspension array;

d) applying the biological sample to the suspension array whereby Tau binds to the capture antibody on the third bead set;

e) adding a first detection antibody to the suspension array, wherein the first detection antibody binds the reference standard and Tau bound to the capture antibody;

f) measuring a first signal from the first detection antibody bound to the reference standard in the first bead set;

g) measuring a second signal from the first detection antibody bound to the reference standard in the second bead set;

h) generating a standard curve based upon the first and second signals; and i) quantitating the amount of Tau in the third bead set by measuring a third signal from the first detection antibody and comparing the third signal to the first and second signal measurements on the standard curve, wherein the reference standard comprises any one of the modified peptides described herein.

Any suitable biological sample can be used in the methods described herein. In one embodiment, the biological sample is blood, serum, plasma, peripheral blood mononuclear cells, peripheral blood lymphocytes, tissue, or cerebrospinal fluid or cell culture supernatants from primary cell culture, tissue slices, or genetically engineered cell line samples.

In one embodiment, the method is performed in a multiwell plate, nitrocellulose filter, glass fiber or on a glass slide. In another embodiment, the first signal and second signal is a signal selected from the group consisting of phycoerytherin, Alexa 532, streptavidin-phycoerythrin, and streptavidin-Alexa 532. In another embodiment, the reference standard is covalently attached to the bead. In another embodiment, the capture antibody is covalently attached to the bead. In another embodiment, the covalent attachment is a carbodiimide bond.

In another aspect, the present invention provides a kit for conducting an immunoassay to detect Tau, the kit comprising any one or more of the peptides or modified peptides described herein, optionally with instructions for use in the methods described herein.

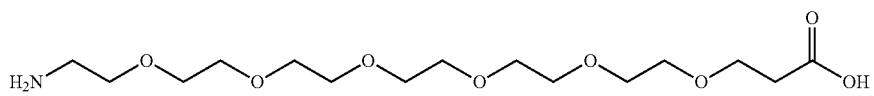

BRIEF DESCRIPTION OF THE DRAWINGS

FIG. 1 shows the six isoforms of Tau found in CSF. See Seq. ID No: 1 to 6.

FIG. 2 shows the structure of an exemplary linker. See Seq. ID No. 35 to 41.

FIG. 3 is a schematic of a sandwich immunoassay.

FIG. 4 is a schematic of a VITROS® immunoassay.

FIG. 5 is a schematic of a Luminex assay.

FIG. 6 shows a typical standard curve obtained using a modified peptide calibrator, (native Tau amino acids (190-209)-(PEG)6-native Tau amino acids (215-230); SEQ ID NO:16)).

FIG. 7 shows the stability of a modified peptide calibrator (native Tau amino acids (190-209)-(PEG)6-native Tau amino acids (215-230); SEQ ID NO:16)) at 2-8° C. over a period of six months.

FIG. 8A depicts the amino acid sequence of the middle region of the Tau protein (i.e., amino acids 126-245), as well as Peptides 9-16, which were created from this region to map the epitope of antibody 9E9. Figure discloses sequences as SEQ ID NOS 42-54, respectively, in order of appearance. FIG. 8B shows the epitope mapping data for antibody 9E9, as assessed by Luminex.

FIG. 9 shows the epitope mapping data for antibody 9E9, as assessed by Biacore.

DETAILED DESCRIPTION OF THE INVENTION

The invention relates to peptides, modified peptides, and compositions that can be used as reference standards and calibrators to measure clinical biomarkers (e.g., Tau) in an immunoassay, as well as methods of measuring the quantity of Tau (e.g., Tau352, Tau381, Tau 383, Tau 410, Tau 412, or Tau 441) in a biological sample. Specifically, the present invention is aimed at creating non-aggregating, non-precipitating, and non-surface-adhering peptide reference standards for Tau for use in immunoassay formats.

I. Definitions

In order that the present disclosure may be more readily understood, certain terms are first defined. Additional definitions are set forth throughout the detailed description.

As used herein, the term "Tau" refers to a microtubule associated protein found in neuronal cells. There are six isoforms of Tau in the human brain resulting from RNA splicing (Himmler, Drechsel et al. 1989). These isoforms differ from one another in having three or four microtubule binding repeats (R) of 31-32 amino acids each in the C-terminal domain, and two, one or none amino terminal inserts (N) of 29 amino acids each (Goedert, Spillantini et al. 1989). Tau can be modified by phosphorylation, glycosylation, and other modifications (Hampel, Blennow et al. 2010). Tau contains repeated C-terminal microtubule binding domains and variable N-terminal domains and differences in the number and type of repeating domains results in the six isoforms (Himmler, Drechsel et al. 1989; Avila, Lucas et al. 2004; Hampel, Blennow et al. 2010). The sequence for the core domain of Tau is identical between the six isoforms and the epitopes used in the design of the present invention are all contained in the core domain, allowing these peptides to represent all six isoforms of Tau (FIG. 1). The amino acid sequences of the six isoforms (Tau 441, Tau 352, Tau 381, Tau 383, Tau 410, and Tau 412) are set forth below in Table 1.

TABLE 1

Tau Peptide Sequences

| Amino Acid Sequence | Description of Peptide/Modified Peptide Sequence |
|---|---|
| (SEQ ID NO: 1)<br>MAEPRQEFEV MEDHAGTYGL GDRKDQGGYT MHQDQEGDTD<br>AGLKESPLQT PTEDGSEEPG SETSDAKSTP TAEDVTAPLV<br>DEGAPGKQAA AQPHTEIPEG TTAEEAGIGD TPSLEDEAAG<br>HVTQARMVSK SKDGTGSDDK KAKGADGKTK IATPRGAAPP<br>GQKGQANATR IPAKTPPAPK TPPSSGEPPK SGDRSGYSSP<br>GSPGTPGSRS RTPSLPTPPT REPKKVAVVR TPPKSPSSAK<br>SRLQTAPVPM PDLKNVKSKI GSTENLKHQP GGGKVQIINK<br>KLDLSNVQSK CGSKDNIKHV PGGGSVQIVY KPVDLSKVTS<br>KCGSLGNIHH KPGGGQVEVK SEKLDFKDRV QSKIGSLDNI<br>THVPGGGNKK IETHKLTFRE NAKAKTDHGA EIVYKSPVVS<br>GDTSPRHLSN VSSTGSIDMV DSPQLATLAD EVSASLAKQG<br>L | Native Tau 441 amino acid sequence |
| (SEQ ID NO: 2)<br>MAEPRQEFEV MEDHAGTYGL GDRKDQGGYT MHQDQEGDTD<br>AGLKESPLQT PTEDGSEEPG SETSDAKSTP TAEDVTAPLV<br>DEGAPGKQAA AQPHTEIPEG TTAEEAGIGD TPSLEDEAAG<br>HVTQARMVSK SKDGTGSDDK KAKGADGKTK IATPRGAAPP<br>GQKGQANATR IPAKTPPAPK TPPSSGEPPK SGDRSGYSSP<br>GSPGTPGSRS RTPSLPTPPT REPKKVAVVR TPPKSPSSAK<br>SRLQTAPVPM PDLKNVKSKI GSTENLKHQP GGGKVQIVYK<br>PVDLSKVTSK CGSLGNIHHK PGGGQVEVKS EKLDFKDRVQ<br>SKIGSLDNIT HVPGGGNKKI ETHKLTFREN AKAKTDHGAE<br>IVYKSPVVSG DTSPRHLSNV SSTGSIDMVD SPQLATLADE<br>VSASLAKQGL | Native Tau 410 amino acid sequence |
| (SEQ ID NO: 3)<br>MAEPRQEFEV MEDHAGTYGL GDRKDQGGYT MHQDQEGDTD<br>AGLKESPLQT PTEDGSEEPG SETSDAKSTP TAEAEEAGIG<br>DTPSLEDEAA GHVTQARMVS KSKDGTGSDD KKAKGADGKT | Native Tau 412 amino acid sequence |

TABLE 1-continued

Tau Peptide Sequences

| Amino Acid Sequence | Description of Peptide/Modified Peptide Sequence |
|---|---|
| KIATPRGAAP PGQKGQANAT RIPAKTPPAP KTPPSSGEPP KSGDRSGYSS PGSPGTPGSR SRTPSLPTPP TREPKKVAVV RTPPKSPSSA KSRLQTAPVP MPDLKNVKSK IGSTENLKHQ PGGGKVQIIN KKLDLSNVQS KCGSKDNIKH VPGGGSVQIV YKPVDLSKVT SKCGSLGNIH HKPGGGQVEV KSEKLDFKDR VQSKIGSLDN ITHVPGGGNK KIETHKLTFR ENAKAKTDHG AEIVYKSPVV SGDTSPRHLS NVSSTGSIDM VDSPQLATLA DEVSASLAKQ GL | |
| (SEQ ID NO: 4) MAEPRQEFEV MEDHAGTYGL GDRKDQGGYT MHQDQEGDTD AGLKESPLQT PTEDGSEEPG SETSDAKSTP TAEAEEAGIG DTPSLEDEAA GHVTQARMVS KSKDGTGSDD KKAKGADGKT KIATPRGAAP PGQKGQANAT RIPAKTPPAP KTPPSSGEPP KSGDRSGYSS PGSPGTPGSR SRTPSLPTPP TREPKKVAVV RTPPKSPSSA KSRLQTAPVP MPDLKNVKSK IGSTENLKHQ PGGGKVQIVY KPVDLSKVTS KCGSLGNIHH KPGGGQVEVK SEKLDFKDRV QSKIGSLDNI THVPGGGNKK IETHKLTFRE NAKAKTDHGA EIVYKSPVVS GDTSPRHLSN VSSTGSIDMV DSPQLATLAD EVSASLAKQG L | Native Tau 381 amino acid sequence |
| (SEQ ID NO: 5) MAEPRQEFEV MEDHAGTYGL GDRKDQGGYT MHQDQEGDTD AGLKAEEAGI GDTPSLEDEA AGHVTQARMV SKSKDGTGSD DKKAKGADGK TKIATPRGAA PPGQKGQANA TRIPAKTPPA PKTPPSSGEP PKSGDRSGYS SPGSPGTPGS RSRTPSLPTP PTREPKKVAV VRTPPKSPSS AKSRLQTAPV PMPDLKNVKS KIGSTENLKH QPGGGKVQII NKKLDLSNVQ SKCGSKDNIK HVPGGGSVQI VYKPVDLSKV TSKCGSLGNI HHKPGGGQVE VKSEKLDFKD RVQSKIGSLD NITHVPGGGN KKIETHKLTF RENAKAKTDH GAEIVYKSPV VSGDTSPRHL SNVSSTGSID MVDSPQLATL ADEVSASLAK QGL | Native Tau 383 amino acid sequence |
| (SEQ ID NO: 6) MAEPRQEFEV MEDHAGTYGL GDRKDQGGYT MHQDQEGDTD AGLKAEEAGI GDTPSLEDEA AGHVTQARMV SKSKDGTGSD DKKAKGADGK TKIATPRGAA PPGQKGQANA TRIPAKTPPA PKTPPSSGEP PKSGDRSGYS SPGSPGTPGS RSRTPSLPTP PTREPKKVAV VRTPPKSPSS AKSRLQTAPV PMPDLKNVKS KIGSTENLKH QPGGGKVQIV YKPVDLSKVT SKCGSLGNIH HKPGGGQVEV KSEKLDFKDR VQSKIGSLDN ITHVPGGGNK KIETHKLTFR ENAKAKTDHG AEIVYKSPVV SGDTSPRHLS NVSSTGSIDM VDSPQLATLA DEVSASLAKQ GL | Native Tau 352 amino acid sequence |

As used herein, the term "antibody" is used in the broadest sense, and specifically covers monoclonal antibodies (including full length monoclonal antibodies or fragments thereof, such as Fab fragments and single chain antibodies), polyclonal antibodies, multispecific antibodies (i.e., bispecific antibodies), and genetically engineered antibodies, including affinity matured antibodies. "Antibody" can also refer to an antibody or antibody fragments fused to carrier proteins/organisms, such as phage or other display carriers, that have the same properties as isolated antibodies.

As used herein, the term "isolated", as used herein with reference to peptides, refers to a preparation of protein or protein complex (e.g., modified peptide molecule) that is essentially free from contaminating proteins normally present with the protein or complex (i.e., in the cellular milieu in which the protein or complex is found endogenously). Thus, an isolated protein complex is isolated from cellular components that normally would "contaminate" or interfere with the study of the peptide or complex in isolation. It is to be understood, however, that such an "isolated" complex may incorporate other proteins the modulation of which, by the protein or protein complex, is being investigated.

As used herein, the term "isolated" as also used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

As used herein, the term "nucleic acid" refers to polynucleotide, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotide. "Nucleic acid" can also refer to a peptide nucleic acid "PNA" or an artificially synthesized DNA or RNA.

As used herein, the term "peptides", "proteins", and "polypeptides" are used interchangeably herein. The term "purified protein" refers to a preparation of protein or proteins that are preferably isolated from or otherwise substantially free of other proteins normally associated with the protein(s) in a cell or cell lysate.

As used herein, the term "modified peptide" refers to a peptide that has been modified relative to the native sequence of that peptide. For example, a modification may include the removal of a deleterious domain or the addition of a linker within the native peptide sequence.

As used herein, the term "binding" refers to direct association between two molecules, due to, for example, covalent, electrostatic, hydrophobic, ionic, and/or hydrogen-bond interactions under physiological conditions. Likewise, "complex formation", between two or more polypeptides, refers to a direct association between polypeptides, due to, for example, covalent, electrostatic, hydrophobic, ionic, and/or hydrogen-bond interactions under physiological conditions.

As used herein, the term "domain" refers to a region of protein that comprises a particular structure and/or performs a particular function (e.g., microtubule binding domain, phosphorylation domain, etc.).

As used herein, the term "immunoreactive domain" refers to a region of protein that comprises a particular amino acid sequence that can be recognized by an antibody. This region includes amino acid sequences that contain modifications such as glycosylation, methylation, phosphorylation, or any other post-translational modifications known to one of ordinary skill in the art. Examples of amino acids that can be phosphorylated are tyrosine, serine, or threonine amino acids. An "immunoreactive domain" that includes amino acids that are phosphorylated would also be characterized as a phosphorylation domain. An "immunoreactive domain" also includes two or more regions of a protein that are in close proximity to one another in the protein's native folded state, which together comprise an antibody binding site.

As used herein, the term "immunoassay" refers to a biochemical test that utilizes one or more antibodies to measure the presence or concentration of an analyte (e.g., Tau) in a biological matrix. This assay can produce a measurable signal in response to a specific binding if an antibody to an immunoreactive domain of a specific protein or peptide.

II. Reference Standards

Provided herein are isolated peptides and modified peptides that can be used as reference standards and calibrators to measure clinical biomarkers (e.g., Tau). In one embodiment, the reference standard comprises an isolated peptide (e.g., an immunoreactive region). In a particular embodiment, the peptide has the amino acid sequence set forth in SEQ ID NO: 7, 8, 9, 10, 11, 12, or 13, as set forth below in Table 2. Phosphorylated regions of Tau can also be used to generate modified peptides for use as reference standards, e.g., peptides having the amino acid sequence set forth in SEQ ID NO: 14 or 15.

TABLE 2

Peptides/Immunoreactive Regions

| Amino Acid Sequence | Description |
|---|---|
| KSGDRSGYSSPGSPGTPGSR (SEQ ID NO: 7) | native Tau amino acids (190-209) |
| RGAAPPGQKGQANATR (SEQ ID NO: 8) | native Tau amino acids (155-170) |
| LPTPPTREPKKVAVVR (SEQ ID NO: 9) | native Tau amino acids (215-230) |
| KTPPSSGEPPKSGDRS (SEQ ID NO: 10) | native Tau amino acids (180-195) |

TABLE 2-continued

Peptides/Immunoreactive Regions

| Amino Acid Sequence | Description |
|---|---|
| SGDRSGYSSP (SEQ ID NO: 11) | native Tau amino acids (191-200) |
| GAAPPGQKGQAN (SEQ ID NO: 12) | native Tau amino acids (156-167) |
| IPAKTPPAPKT(PO$_4$)PPSSGEPPK (SEQ ID NO: 13) | native Tau amino acids (171-190); amino acid T181 is phosphorylated |
| REPKKVAVVRT(PO$_4$)PPKSPSSAK (SEQ ID NO: 14) | native Tau amino acids (221-240); amino acid T231 is phosphorylated |

*All amino acid numbers for the peptides correspond to the Tau 441 sequence.

In another embodiment, the reference standard is a modified peptide, e.g., comprising a linker, a deletion, or substitution in an immunoreactive and/or non-immunoreactive domain. For example, in one embodiment, the modified peptide comprises an N-terminal immunoreactive region, a C-terminal immunoreactive region and a linker region, wherein the immunoreactive regions are defined by particular amino acid sequences. In another embodiment, the modified peptide comprises an N-terminal immunoreactive region, a C-terminal immunoreactive region, and a linker region, wherein:

(a) the N-terminal immunoreactive region comprises or has an amino acid sequence selected from the group consisting of SEQ ID NOs: 7, 8, 9, and 10; and/or (b) the C-terminal immunoreactive region comprises or has an amino acid sequence selected from the group consisting of SEQ ID NOs: 7, 8, 9, and 10, and wherein the N-terminal and C-terminal immunoreactive regions are different amino acid sequences.

In another embodiment, the modified peptide comprises N-terminal and C-terminal immunoreactive regions comprising or having amino acid sequences selected from the group consisting of SEQ ID NOs:7 and 9, SEQ ID NOs:7 and 8, SEQ ID NOs:8 and 9, and SEQ ID NOs:9 and 10, respectively. In another embodiment, the N-terminal and C-terminal immunoreactive regions comprise or have the amino acid sequences set forth in SEQ ID NOs:7 and 9, respectively. In a particular embodiment, the modified peptide is: KSGDRSGYSSPGSPGTPGSR-Generic Linker-LPTPPTREPKKVAVVR (SEQ ID NO: 16). In another embodiment, the modified peptide is: RGAAPPGQK-GQANATR-Generic Linker-KSGDRSGYSSPGSPGT-PGSR (SEQ ID NO:17), RGAAPPGQKGQANATR-Generic Linker-LPTPPTREPKKVAVVR (SEQ ID NO:18), or KTPPSSGEPPKSGDRS-Generic Linker-LPTPPTREPKK-VAVVR (SEQ ID NO:19).

In another embodiment, the modified peptide comprises an N-terminal immunoreactive region, a C-terminal immunoreactive region, and a linker region, wherein:

(a) the N-terminal immunoreactive region comprises or has the amino acid sequence set forth in SEQ ID NO:7 and the C-terminal immunoreactive region comprises or has the amino acid sequence set forth in SEQ ID NO:9;

(b) the N-terminal immunoreactive region comprises or has the amino acid sequence set forth in SEQ ID NO:8 and the C-terminal immunoreactive region comprises or has the amino acid sequence set forth in SEQ ID NO:7;

(c) the N-terminal immunoreactive region comprises or has the amino acid sequence set forth in SEQ ID NO:8 and the C-terminal immunoreactive region comprises or has the amino acid sequence set forth in SEQ ID NO:9;

(d) the N-terminal immunoreactive region comprises or has the amino acid sequence set forth in SEQ ID NO:10 and the C-terminal immunoreactive region comprises or has the amino acid sequence set forth in SEQ ID NO:9;

(e) the N-terminal immunoreactive region comprises or has the amino acid sequence set forth in SEQ ID NO:7 and the C-terminal immunoreactive region comprises or has the amino acid sequence set forth in SEQ ID NO:8;

(f) the N-terminal immunoreactive region comprises or has the amino acid sequence set forth in SEQ ID NO:9 and the C-terminal immunoreactive region comprises or has the amino acid sequence set forth in SEQ ID NO:7;

(g) the N-terminal immunoreactive region comprises or has the amino acid sequence set forth in SEQ ID NO:9 and the C-terminal immunoreactive region comprises or has the amino acid sequence set forth in SEQ ID NO:8;

(h) the N-terminal immunoreactive region comprises or has the amino acid sequence set forth in SEQ ID NO:12 and the C-terminal immunoreactive region comprises or has the amino acid sequence set forth in SEQ ID NO:14;

(i) the N-terminal immunoreactive region comprises or has the amino acid sequence set forth in SEQ ID NO:12 and the C-terminal immunoreactive region comprises or has the amino acid sequence set forth in SEQ ID NO:11;

(j) the N-terminal immunoreactive region comprises or has the amino acid sequence set forth in SEQ ID NO:13 and the C-terminal immunoreactive region comprises or has the amino acid sequence set forth in SEQ ID NO:15; or (k) the N-terminal immunoreactive region comprises or has the amino acid sequence set forth in SEQ ID NO:15 and the C-terminal immunoreactive region comprises or has the amino acid sequence set forth in SEQ ID NO:14.

In a particular embodiment, the N-terminal and C-terminal immunoreactive regions comprise or have the amino acid sequences set forth in SEQ ID NOs: 7 and 9, respectively.

In another embodiment, the modified peptide is shown below in Table 3:

TABLE 3

Modified Peptides/Constructs

| Amino Acid Sequence | Description of Peptide/Modified Peptide Sequence |
|---|---|
| KSGDRSGYSSPGSPGTPGSR-Generic Linker-LPTPPTREPKKVAVVR (SEQ ID NO: 16) | native Tau amino acids (190-209)-Generic Linker-native Tau amino acids (215-230) |
| RGAAPPGQKGQANATR-Generic Linker-KSGDRSGYSSPGSPGTPGSR (SEQ ID NO: 17) | native Tau amino acids (155-170)-Generic Linker-native Tau amino acids (190-209) |
| RGAAPPGQKGQANATR-Generic Linker -LPTPPTREPKKVAVVR (SEQ ID NO: 18) | native Tau amino acids (155-170)-Generic Linker-native Tau amino acids (215-230) |
| KTPPSSGEPPKSGDRS-Generic Linker-LPTPPTREPKKVAVVR (SEQ ID NO: 19) | native Tau amino acids (180-195)-Generic Linker-native Tau amino acids (215-230) |
| RGAAPPGQKGQANATR-(PEG)6-KSGDRSGYSSPGSPGTPGSR (SEQ ID NO: 20) | native Tau amino acids (155-170)-(PEG)6-native Tau amino acids (190-209) |
| RGAAPPGQKGQANATRGGSGGSKS GDRSGYSSPGSPGTPGSR (SEQ ID NO: 21) | native Tau amino acids (155-170)-GGSGGS-native Tau amino acids (190-209) |
| KSGDRSGYSSPGSPGTPGSR-(PEG)6-RGAAPPGQKGQANATR (SEQ ID NO: 22) | native Tau amino acids (190-209)-(PEG)6-native Tau amino acids (155-170) |
| KSGDRSGYSSPGSPGTPGSR-GGSG GS-RGAAPPGQKGQANATR (SEQ ID NO: 23) | native Tau amino acids (190-209)-GGSGGS-native Tau amino acids (155-170) |
| KSGDRSGYSSPGSPGTPGSR-(PEG)6-LPTPPTREPKKVAVVR (SEQ ID NO: 24) | native Tau amino acids (190-209)-(PEG)6-native Tau amino acids (215-230) |
| KSGDRSGYSSPGSPGTPGSR-GGSGGS-LPTPPTREPKKVAVVR (SEQ ID NO: 25) | native Tau amino acids (190-209)-GGSGGS-native Tau amino acids (215-230) |
| LPTPPTREPKKVAVVR-(PEG)6-KSGDRSGYSSPGSPGTPGSR (SEQ ID NO: 26) | native Tau amino acids (215-230)-(PEG)6-native Tau amino acids (190-209) |
| LPTPPTREPKKVAVVR-GGSGGS-KSGDRSGYSSPGSPGTPGSR (SEQ ID NO: 27) | native Tau amino acids (215-230)-GGSGGS-native Tau amino acids (190-209) |

TABLE 3-continued

Modified Peptides/Constructs

| Amino Acid Sequence | Description of Peptide/Modified Peptide Sequence |
|---|---|
| RGAAPPGQKGQANATR-GGSGGS-LPTPPTREPKKVAVVR (SEQ ID NO: 28) | native Tau amino acids (155-170)-GGSGGS-native Tau amino acids (215-230) |
| LPTPPTREPKKVAVVR-(PEG)6-RGAAPPGQKGQANATR (SEQ ID NO: 29) | native Tau amino acids (215-230)-(PEG)6-native Tau amino acids (155-170) |
| LPTPPTREPKKVAVVR-GGSGGS-RGAAPPGQKGQANATR (SEQ ID NO: 30) | native Tau amino acids (215-230)-GGSGGS-native Tau amino acids (155-170) |
| KSGDRSGYSSPGSPGTPGSR-Generic Linker-RGAAPPGQKGQANATR (SEQ ID NO: 31) | native Tau amino acids (190-209)-Generic Linker-native Tau amino acids (155-170) |
| LPTPPTREPKKVAVVR-Generic Linker-KSGDRSGYSSPGSPGTPGSR (SEQ ID NO: 32) | native Tau amino acids (215-230)-Generic Linker-native Tau amino acids (190-209) |
| RGAAPPGQKGQANATR-Generic Linker-LPTPPTREPKKVAVVR (SEQ ID NO: 33) | native Tau amino acids (155-170)-Generic Linker-native Tau amino acids (215-230) |
| LPTPPTREPKKVAVVR-Generic Linker-RGAAPPGQKGQANATR (SEQ ID NO: 34) | native Tau amino acids (215-230)-Generic Linker-native Tau amino acids (155-170) |
| GAAPPGQKGQAN-Generic Linker-REPKKVAVVRT(PO$_4$)PPKSPSSAK (SEQ ID NO: 35) | native Tau amino acids (156-167)-generic linker-native Tau amino acids (221-240); amino acid T231 is phosphorylated |
| GAAPPGQKGQAN-Generic Linker-SGDRSGYSSP (SEQ ID NO: 36) | native Tau amino acids (156-167)-generic linker-native Tau amino acids (191-200) |
| IPAKTPPAPKT(PO$_4$)PPSSGEPPK-Generic Linker-SGDRSGYSSP (SEQ ID NO: 37) | native Tau amino acids (171-190)-generic linker-native Tau amino acids (191-200); amino acid T180 is phosphorylated |
| SGDRSGYSSP-Generic Linker-REPKKVAVVRT(PO$_4$)PPKSPSSAK (SEQ ID NO: 38) | native Tau amino acids (191-200)-generic linker-native Tau amino acids (221-240); amino acid T231 is phosphorylated |

*All amino acid numbers for the modified peptides correspond to the Tau 441 sequence.

The performance of the reference standards (e.g., immunoassay reference standards) or calibrators described herein should have comparable performance to native Tau in an immunoassay. Recombinant full length Tau proteins can be purchased commercially from a number of vendors as a catalog item (Signal Chem and rPeptide). Standard methods can be used to verify the abundance of the full length protein (Smith, Krohn et al., 1985). Additionally, standard methods can be used to verify the abundance of the full length construction from truncated species using mass spectrometry techniques, such as amino acid analysis, that are well known in the field (Kanu et al., 2008).

III. Linkers

Any suitable linker region can be used in the modified peptides described herein (e.g., to link two peptides or immunoreactive regions). In one embodiment, amino acids that do not aggregate are contemplated as the linker. In another embodiment, the amino acids that do not aggregate are in the form of a hydrophilic spacer. In another embodiment, a series of charged residues are used as a linker between the two immunoreactive regions. In another embodiment, any polymer with chemistry able to couple to amino acid residues is used as a linker or spacer. This polymer includes linear polymers, as well as those of known branched topology, such as dendrimers and branched co-polymers.

In one embodiment, the bond between the peptide backbone and linker comprises a covalent bond, avidin-biotin complex or any other stable bond. In another embodiment, the construct does not lead to self-aggregation or nonspecific absorption to laboratory plastics, in particular polypropylene, polystyrene, polycarbonate and other laboratory plastic resins of which pipette tips, tubes, plates and other vessels that hold fluids in which the analyte of interest can be measured.

Exemplary linkers include, but are not limited to, polyethylene glycol, a glutamic acid residue, a glycine residue, a serine residue, an alanine residue, a lysine residue, a lipid, a globular protein, a nucleic acid (including but not limited to DNA, RNA, and PNA), an alkyl chain, or any other linkage that adds to the stability of the two peptides of interest in the immunoassay.

In one embodiment, various forms of polyethylene glycol (PEG) are used as a linker. In a particular embodiment, PEG6 is used to join two peptides. In one embodiment, the linker region comprises a PEG6 linker, e.g., having the following structure:

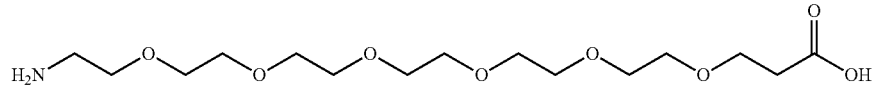 [SMILES: NCCOCCOCCOCCOCCOCCOCCC(=O)O]

In another embodiment, the linker region comprises or has the amino acid sequence set forth in SEQ ID NO:40 (GGSGGS). In another embodiment, the linker region is a non-immunoreactive domain.

IV. Methods

Provided herein are methods for generating a peptide, modified peptide, or compositions thereof, as well as methods of using the same as a reference standard or calibrator (e.g., in an immunoassay) to measure the abundance of an analyte (e.g., Tau 352, Tau 381, Tau 383, Tau 410, Tau 412, or Tau 441) in a biological sample (e.g., blood, serum, plasma, peripheral blood mononuclear cells, peripheral blood lymphocytes tissue, cerebrospinal fluid or cells). In one aspect, the invention relates to methods of measuring the clinical markers (e.g., Tau) with the reference standards of the invention using, for example, an immunoassay.

An immunoassay often requires biologically specific capture reagents, such as antibodies, to capture the analytes or biomarkers of interest (e.g., Tau). Antibodies can be produced by methods well known in the art, e.g., by immunizing animals with the biomarkers as antigens. Biomarkers can be isolated from samples based on their binding characteristics. Alternatively, if the amino acid sequence of a polypeptide biomarker is known, the polypeptide can be synthesized and used to generate antibodies by methods well known in the art. Examples of biomarkers include, but are not limited to Tau peptides and phosphorylated Tau peptides.

Exemplary immunoassays include, for example, sandwich immunoassays, such as ELISAs (Enzyme-Linked ImmunoSorbent Assays) or fluorescence-based immunoassays, as well as other enzyme immunoassays. In one embodiment, the immunoassay is a SELDI-based immunoassay, wherein a biospecific capture reagent for the biomarker is attached to the surface of a mass spectrometry (MS) probe, such as a pre-activated PROTEINCHIP® array. The biomarker is then specifically captured on the biochip through this reagent, and the captured biomarker is detected by mass spectrometry.

In another embodiment, the immunoassay is a single antibody immunoassay, often run in a competitive or "competition" mode for immunoreactive binding sites to measure Tau in a biological sample. For example, a single antibody specific to Tau is immobilized to a solid surface, such as a well in a microtiter plate, a bead, or other immunoassay relevant surface. The antibody can be covalently linked via many different methods, such as EDC mediated linkage of carboxyl and amine groups, or via passive absorbance or through a Protein A or Protein G interface. A Tau competitor is then generated from a Tau standard or calibrator containing the full length Tau peptide or a modified version that retains the epitope of the capture antibody. The Tau competitor is used to generate competition between the native Tau in the biological sample and the binding site (paratope) on the immobilized antibody. A paratope is a term used to describe the binding region of the antibody that recognizes the epitope or immunoreactive domain on the analyte. The Tau competitor is tagged for detection purposes. In one embodiment, the tag is an enzyme, such as horseradish peroxidase or alkaline phosphatase. In another embodiment, the tag is a fluorescein such as phycoerythrin. In yet another embodiment, the tag is another tag, such as biotin or ruthenium. In yet another embodiment, the tag is a nucleic acid such as DNA, RNA or PNA, where by detection of the antibody is quantitated using sensitive technology to detect the nucleic acid flag, such as Polymerase Chain Reaction (PCR). A single concentration of the Tau competitor is used in the assay and would be determined based on the ability to compete with the natural levels of Tau found in biological samples.

In another embodiment, the immunoassay is a double sandwich immunoassay or ELISA (see, e.g., FIG. 3). For example, the immunoassay is a sandwich immunoassay, wherein the capture antibody is biotinylated and the reporter (detection) antibody is conjugated to horseradish peroxidase (HRP). These two antibodies are mixed with Tau peptides or CSF and incubated. The well is washed and detection occurs through enhanced chemiluminescence. Traditional assay formats for these assays include ELISA techniques that provide quantitation suitable for the analysis of clinical samples. However, they are often limited to one biomarker assay per well. Newer technologies have been developed that allow multiple biomarkers to be analyzed in a single well or reaction vessel. Some of the multiplexed technologies utilize antibodies spotted onto a solid surface such as glass slides or specialized microtiter plates.

In another aspect, the immunoassay is an intra-assay calibration system. In this approach, an immunoassay format, such as the Ortho Clinical Diagnostics VITROS® system (see, e.g., FIG. 4), the Luminex bead based system (see, e.g., FIG. 5), or the Meso-Scale Discovery ECL plate based system is used. Peptides containing amino acid residues that encompass the antibody binding epitope of the detection antibody are generated. In one embodiment, these peptides include modifications that enable them to be covalently coupled to a solid phase or modifications that increase their solubility and use in aqueous immunoassays. These peptides are immobilized at different concentrations to the relevant solid phase as defined by multiplexed immunoassay systems, to create a set of well-defined standards from which to create a standard curve.

In one embodiment, the suspension array technology is the Luminex xMAP technology. Luminex xMAP technology uses latex beads that contain a ratio of two fluorescent dyes. Different bead "sets" are created by altering the ratio of these two dyes. The beads are mixed together to form a suspension array. The bead mixture is analyzed by an instrument that identifies each bead by the fluorescence ratio as it passes in front of a laser. These bead sets have different modifications on their surface that are used for the covalent attachment of molecules such as proteins, peptides, antibodies, etc. This allows the assay to be performed on the surface of these beads. Assays are quantitated through the incorporation of a third fluorescent label, such as phycoerythrin to a reporter antibody directed at the analyte of interest (e.g., Tau). A second laser in the instrument measures the fluorescence of this reporter label as the beads move through the instrument.

In one embodiment, the method comprises:
a) attaching a reference standard to at least two beads thereby forming a first bead set and a second bead set, wherein the reference standard comprises an epitope recognized by a first detection antibody and wherein each bead set comprises a different concentration of the reference standard;
b) attaching a capture antibody specific to Tau to a third bead set;
c) combining the bead sets together to form a suspension array;
d) applying the biological sample to the suspension array whereby Tau binds to the capture antibody on the third bead set;
e) adding a first detection antibody to the suspension array, wherein the first detection antibody binds the reference standard and Tau bound to the capture antibody;
f) measuring a first signal from the first detection antibody bound to the reference standard in the first bead set;
g) measuring a second signal from the first detection antibody bound to the reference standard in the second bead set;
h) generating a standard curve based upon the first and second signals; and
i) quantitating the amount of Tau in the third bead set by measuring a third signal from the first detection antibody and comparing the third signal to the first and second signal measurements on the standard curve, wherein the reference standard comprises any one of the compositions described herein.

In another embodiment, the assay is made quantitative by establishing a calibration curve. In another embodiment, quantitation is performed by making a set of Tau standards or calibrators that are either the full length Tau peptide or a modified version that retains the epitope of the capture antibody. These untagged standards or calibrators are prepared in either buffer or a biological matrix that does not contain Tau. In one embodiment, the calibration curve is established by mixing one of the concentrations of the untagged standards or calibrators with the tagged Tau competitor to the immobilized antibody. The resulting signal value from each tested concentration of untagged standard or calibrator is used to generate a standard curve; plotting the concentration of the untagged Tau standards or calibrators versus the resulting signal values. Once a standard quantitative curve is established, an assay is used to determine the levels of Tau in biological samples by mixing the tagged Tau competitor at the same fixed concentration with the biological sample. The resulting signal value is plotted on the standard curve to determine the level of Tau in the biological sample.

The analyte and/or reference standard may be bound to a variety of surfaces. A surface can be any solid phase surface to which an antibody or reference standard can be immobilized by covalent linkage, passive absorbance, biotin-streptavidin or any other linkage known to one of ordinary skill in the art. For example, the surface may be a bead, plate, slides, fiber, surface plasmon resonance sensors or any solid surface.

In another embodiment, the method is performed in a multi-well plate, nitrocellulose filter or on a glass slide. In another embodiment, the first and second signals are detected by fluorescence. For example, the first signal and second signal may be a signal selected from the group consisting of phycoerythrin, alexa 532, streptavidin-phycoerythrin and streptavidin-Alexa 532. In another embodiment, the signal is detected by enzymatic activity (i.e., horseradish peroxidase or alkaline phosphatase), chemiluminescence, radioactivity, infra-red emission, fluorescence resonance energy transfer (FRET) or any other method known to one of ordinary skill in the art.

V. Kits

In another aspect, the invention provides a kit for conducting an immunoassay to detect a Tau peptide, wherein the kit comprise a reference standard (e.g., peptide, modified peptide, or composition) of the invention. The kits may include a label indicating the intended use of the contents of the kit (e.g., in the methods described herein). The term label includes any writing, marketing materials or recorded material supplied on or with the kit, or which otherwise accompanies the kit.

The present invention is further illustrated by the following examples which should not be construed as limiting. The entire contents of Sequence Listing, Figures and all references, patents and published patent applications cited throughout this application are expressly incorporated herein by reference.

EXAMPLES

Materials

All full length recombinant Tau proteins were obtained from SignalChem (SC, cat # T08-54N)) as a 0.2 mg/mL stock in Phosphate Buffered Saline (PBS), pH 7.4 or 50 mM Tris, pH 7.5, containing 150 mM NaCl, 0.25 mM DTT, o.1 mM PMSF, 25% glycerol. All modified peptides were received as lyophilized powder and were obtained from The American Peptide Company (AP), BaChem (BC), and Anaspec (AN). These peptides were synthesized using solid phase methods known to those skilled in the art (see, for example, Barany, G. et al., Gross, E. et al., (1980); and Stewart, et al. (1984).

Stability of a Tau peptide, native Tau amino acids (190-209)-(PEG)6-native Tau amino acids (215-230); (SEQ ID NO:16) was measured by storing the dissolved peptides at 2-8° C. and −20° C. and periodically measuring the signal given by the peptides in a sandwich immunoassay. As shown in FIG. 7, the peptide is stable for at least 6 months when stored at 2-8° C. In this particular assay, the antibody reagents lose activity over time. In order to account for this, the signal for the peptides stored at 2-8° C. was normalized to the signal for the peptides stored at −20° C.

Mouse anti-Tau antibodies (1A4.C3 and F11-1-1) were obtained via protein-G purification of culture supernatants produced by the relevant hybridoma cell lines. Phycoerythrin-streptavidin conjugate was obtained from Jackson Immunoresearch (West Grove, Pa.). Tween-20, 1-ethyl-3-[3 dimethylaminopropyl]carbodiimide hydrochloride (EDC), sodium azide, IgG free Bovine Serum Albumin 10 (BSA), and sodium phosphate were purchased from Sigma-Aldrich Corporation (St. Louis, Mo.). Phosphate buffered saline (PBS) was obtained from Mediatech Incorporated (Herndon, Va.). Carboxylated Luminex beads were purchased from Bio-Rad Incorporated (Hercules, Calif.). Phycoerythrin label goat anti-mouse IgG antibody was obtained from Jackson Immunoresearch (West Grove, Pa.).

Example 1

VITROS® Immunoassay

A schematic of a VITROS® immunoassay is shown in FIG. 4. Briefly, a biological sample (human CSF) was added to a VITROS® microwell coated with streptavidin (Ortho Clinical Diagnostics, Rochester, N.Y. (OCD). A biotin labeled anti-Tau antibody (mouse monoclonal anti-Tau) was added next, followed by a second horseradish peroxidase tagged (HRP)-labeled antibody (mouse monoclonal anti-Tau), completing the sandwich. Both antibodies are specific to a different sequence within the core domain that is common between all six isoforms of Tau. Additionally, a reference standard Tau peptide (e.g., reference standard Tau 441 (SEQ ID NO. 1) or a modified Tau reference standard (e.g., as set forth in Table 3) was added to a VITROS® microwell coated with streptavidin (Ortho Clinical Diagnostics, Rochester, N.Y. (OCD)). A biotin labeled anti-Tau antibody was added next, followed by a second horseradish peroxidase tagged (HRP) antibody, completing the sandwich. The wells were then incubated 30 minutes at 37° C. to allow Tau 441, Tau reference peptides, or Tau in CSF to be bound by the antibodies, forming a sandwich on the surface of the microwell (e.g., the Tau-antibody complex is captured by the streptavidin on the microwell). Unbound materials were removed by washing.

The bound HRP conjugate was then measured by a luminescent reaction. Specifically, a reagent containing luminogenic substrates (a luminol derivative and a peracid salt) and an electron transfer agent were added to the wells. The HRP in the bound conjugate catalyzes the oxidation of the luminol derivative, producing light. The electron transfer agent (a substituted acetanilide) increases the level of light produced and prolongs its emission. The light signals were then detected on a Vitros ECiQ clinical analyzer using an enhanced chemiluminescent substrate. The raw luminescence units (ALU) measured by the instrument were fit to a 4-parameter logistic model to create a standard curve, as described below in Example 3. The amount of HRP conjugate bound is directly proportional to the concentration of Tau present. The measured concentrations of Tau in human CSF samples are shown in Table 4, as set forth below.

TABLE 4

Tau Levels Measured in Human CSF

| CSF | Diagnosis | Vitros Tau (pg/mL) |
| --- | --- | --- |
| 1 | AD | 1440 |
| 2 | AD | 1057 |
| 3 | AD | 861 |
| 4 | AD | 1010 |
| 5 | AD | 977 |
| 6 | Normal | 351 |
| 7 | Normal | 354 |
| 8 | Normal | 217 |
| 9 | Normal | 196 |
| 10 | Normal | 419 |

In a specific example, a modified Tau peptide, native Tau amino acids (190-209)-(PEG)6-native Tau amino acids (215-230); (SEQ ID NO:16)) was used as a reference standard. The standard curve generated using is described in further detail below in Example 3 and is shown in FIG. 6.

Example 2

Intra-Assay Bead Approach

FIG. 5 illustrates the Tau intra-assay bead approach (i.e., a Luminex assay). Bead sets coupled with different concentrations of Tau standard peptides (or other native or modified Tau peptides) were combined with a bead set coupled with an anti-Tau specific capture antibody to form a suspension array. The array was incubated with a biological sample, where the Tau peptide in the biological sample was captured by the bead coupled with anti-Tau capture antibody. A tagged detection antibody specific to a separate sequence within the core domain of the Tau peptide was added to the suspension array, thereby binding to the captured Tau peptide and also to the beads that have Tau peptides coupled to their surface. The MFI values obtained from the beads with Tau peptides coupled to their surface were used to generate an intra-assay calibration curve. The amount of Tau in the biological sample was determined from the amount of captured Tau on the bead coupled with the anti-Tau capture using an intra-assay standard curve.

Example 3

Calibration Curve

To determine the amount of Tau in a biological sample using the sandwich based assay described in Example 1, a calibration curve was created. Specifically, a calibration curve was generated by harmonizing the signal given by the modified peptide (Table 3, native Tau amino acids (190-209)-(PEG)6-native Tau amino acids (215-230)) with that given by native Tau 441 (Table 1, SEQ ID NO: 1) in a buffer matrix. Briefly, a standard curve was generated by first diluting the modified peptide into calibrator matrix at specific concentration levels within the linear range of the assay. The modified peptides are diluted to a corresponding molar equivalent of native Tau 441 while taking the percent peptide, purity, and molecular mass of the modified peptide and the purity of native Tau 441 into account. The levels of the modified peptide were then run in the immunoassay as described in Example 1, along with a separate set of native calibrator standards made with recombinant Tau 441 (Table 1, SEQ ID 1). The raw ALU values generated from the synthetic tau peptides were fit to the native Tau 441 standard curve and a concentration equivalent to Tau 441 (pg/mL) was assigned for each modified peptide level. These assigned values for the modified peptides were then plotted against ALU to generate the calibration curve. This calibration curve was then used to measure the levels of Tau in a biological fluid. A modified peptide calibration curve generated as described in Example 1 is shown in FIG. 6.

Example 4

Epitope Mapping for Anti-Tau Antibody 9E9 by Luminex Method

FIG. 8A shows the amino acid sequence of the middle region of the Tau protein (i.e., from amino acids 126-245).

Peptides 9-16 were created from this region of Tau. These peptides were 20 amino acids in length and overlapped by 5 amino acids down the length of the Tau sequence.

Peptides 9-16, as well as peptides consisting of known epitopes for commercially available antibodies (BT2, HT7, Tau 5, and Tau1), were fused to luminex beads using standard amine couple chemistries. For epitope mapping, purified antibodies were incubated with the luminex bead sets and run on a Bioplex 100 instrument.

As shown in FIG. 8B, antibody 9E9 bound only to peptide 13 and not the BT2 peptide or peptide 14.

Example 5

Epitope Mapping of Anti-Tau Antibody 9E9 by Biacore

Antibody 9E9 also was characterized using Biacore T100 (immobilized to the CM5 gold surface by amino coupling). 9E9 (10 μg/mL in 10 Mm Sodium Acetate Buffer) was injected onto active CM5 at 1-ul/min for seven minutes to a final immobilization of 10000RU. The surface was then deactivated by passage of 1 M ethanolamine. Short 8 AA long peptides spanning the region from AA 186-199 (peptide overlay) were flowed over the chip for binding activity. Specifically, recombinant Tau 441 (positive control) (final conc. 25 nM) followed by IL-23 (negative control), and peptides 15-17 at two concentrations, 25 μg/mL and 125 μg/mL. The surface was regenerated by a 30 ul/min of Glycine pH 1.75. Dilutions were prepared using 1×HBS-EP buffer. Data was analyzed using Biacore Evaluation software 1.0.

As shown in FIG. 9, Peptide 16 was the only peptide that generated a response with two different concentrations of 9E9 antibody, thereby narrowing down the binding epitope to amino acids 189-196.

SUMMARY OF SEQUENCE LISTING

| Amino Acid Sequence | Description of Peptide/Modified Peptide Sequence |
|---|---|
| (SEQ ID NO: 1) | Native Tau 441 amino acid sequence |
| (SEQ ID NO: 2) | Native Tau 410 amino acid sequence |
| (SEQ ID NO: 3) | Native Tau 412 amino acid sequence |
| (SEQ ID NO: 4) | Native Tau 381 amino acid sequence |
| (SEQ ID NO: 5) | Native Tau 383 amino acid sequence |
| (SEQ ID NO: 6) | Native Tau 352 amino acid sequence |
| (SEQ ID NO: 7) | Native Tau amino acids (190-209) |
| (SEQ ID NO: 8) | Native Tau amino acids (155-170) |
| (SEQ ID NO: 9) | Native Tau amino acids (215-230) |
| (SEQ ID NO: 10) | Native Tau amino acids (180-195) |
| (SEQ ID NO: 11) | Native Tau amino acids (191-200) |
| (SEQ ID NO: 12) | Native Tau amino acids (156-167) |
| (SEQ ID NO: 13) | Native Tau amino acids (171-190) |
| (SEQ ID NO: 14) | Native Tau amino acids (221-240); amino acid T231 is phosphorylated |
| (SEQ ID NO: 16) | Native Tau amino acids (190-209)-generic-native Tau amino acids (215-230) |
| (SEQ ID NO: 17) | Native Tau amino acids (155-170)-generic-native Tau amino acids (190-209) |
| (SEQ ID NO: 18) | Native Tau amino acids (155-170)-generic-native Tau amino acids (215-230) |
| (SEQ ID NO: 19) | Native Tau amino acids (180-195) - (PEG)6-native Tau amino acids (215-230) |
| (SEQ ID NO: 20) | Native Tau amino acids (155-170)-(PEG)6-native Tau amino acids (190-209) |
| (SEQ ID NO: 21) | Native Tau amino acids (155-170)-GGSGGS-native Tau amino acids (190-209) |
| (SEQ ID NO: 22) | Native Tau amino acids (190-209)-(PEG)6-native Tau amino acids (155-170) |
| (SEQ ID NO: 23) | Native Tau amino acids (190-209)-GGSGGS-native Tau amino acids (155-170) |
| (SEQ ID NO: 24) | Native Tau amino acids (190-209)-(PEG)6-native Tau amino acids (215-230) |
| (SEQ ID NO: 25) | Native Tau amino acids (190-209)-GGSGGS-native Tau amino acids (215-230) |
| (SEQ ID NO: 26) | Native Tau amino acids (215-230)-(PEG)6-native Tau amino acids (190-209) |
| (SEQ ID NO: 27) | Native Tau amino acids (215-230)-GGSGGS-native Tau amino acids (190-209) |
| (SEQ ID NO: 28) | Native Tau amino acids (155-170)-GGSGGS-native Tau amino acids (215-230) |
| (SEQ ID NO: 29) | Native Tau amino acids (215-230)-(PEG)6-native Tau amino acids (155-170) |
| (SEQ ID NO: 30) | Native Tau amino acids (215-230)-GGSGGS-native Tau amino acids (155-170) |
| (SEQ ID NO: 31) | Native Tau amino acids (190-209)-generic-native Tau amino acids (155-170) |
| (SEQ ID NO: 32) | Native Tau amino acids (215-230)-generic-native Tau amino acids (190-209) |
| (SEQ ID NO: 33) | Native Tau amino acids (155-170)-generic-native Tau amino acids (215-230) |
| (SEQ ID NO: 34) | Native Tau amino acids (215-230)-generic-native Tau amino acids (155-170) |
| (SEQ ID NO: 35) | Native Tau amino acids (156-167)-generic linker-native Tau amino acids (221-240); amino acid T231 is phosphorylated |
| (SEQ ID NO: 36) | Native Tau amino acids (156-167)-generic linker-native Tau amino acids (191-200) |
| (SEQ ID NO: 37) | Native Tau amino acids (171-190)-generic linker-native Tau amino acids (191-200); amino acid T180 is phosphorylated |
| (SEQ ID NO: 38) | Native Tau amino acids (191-200)-generic linker-native Tau amino acids (221-240); amino acid T231 is phosphorylated |
| (SEQ ID NO: 39) | A-B)-Generic Linker-(X-Y) Generic A, B, X, Y, Linker to be specified |
| (SEQ ID NO: 40) | Peptide Linker |
| (SEQ ID NO: 41) | PEG6 Linker |

REFERENCES

Avila, J., J. J. Lucas, et al. (2004). "Role of Tau protein in both physiological and pathological conditions." *Physiol Rev* 84(2): 361-384.

Barany, G. et al., *The Peptides: Analysis, Synthesis, Biology—Special Methods in Peptide Synthesis Part A*, Vol. 2, pp. 3-284.

Friedhoff, P., M. von Bergen, et al. (2000). "Structure of Tau protein and assembly into paired helical filaments." *Biochim Biophys Acta* 1502(1): 122-132.

Goedert, M., M. G. Spillantini, et al. (1989). "Multiple isoforms of human microtubule-associated protein Tau: sequences and localization in neurofibrillary tangles of Alzheimer's disease." *Neuron* 3(4): 519-526.

Gross, E. et al., eds., Academic Press, New York, (1980); 25.

Hampel, H., K. Blennow, et al. (2010). "Total and phosphorylated Tau protein as biological markers of Alzheimer's disease." *Exp Gerontol* 45(1): 30-40.

Hampel, H., R. Frank, et al. (2010). "Biomarkers for Alzheimer's disease: academic, industry and regulatory perspectives." *Nat Rev Drug Discov* 9(7): 560-574.

Hanisch, K., H. Soininen, et al. (2010). "Analysis of human Tau in cerebrospinal fluid." *J Proteome Res* 9(3): 1476-1482.

Himmler, A., D. Drechsel, et al. (1989). "Tau consists of a set of proteins with repeated C-terminal microtubule-binding domains and variable N-terminal domains." *Mol Cell Biol* 9(4): 1381-1388.

Jeganathan, S., M. von Bergen, et al. (2006). "Global hairpin folding of Tau in solution." *Biochemistry* 45(7): 2283-2293.

Johnson, G. V., P. Seubert, et al. (1997). "The Tau protein in human cerebrospinal fluid in Alzheimer's disease consists of proteolytically derived fragments." *J Neurochem* 68(1): 430-433.

Kanu et al., "Ion mobility-mass spectrometry" *Journal of Mass Spectrometry*, 43(1): 1-22 (2008).

Mattsson, N. and H. Zetterberg (2009). "Alzheimer's disease and CSF biomarkers: key challenges for broad clinical applications." *Biomark Med* 3(6): 735-737.

Mattsson, N., H. Zetterberg, et al. (2009). "CSF biomarkers and incipient Alzheimer disease in patients with mild cognitive impairment." *JAMA* 302(4): 385-393.

Mukrasch, M. D., S. Bibow, et al. (2009). "Structural polymorphism of 441-residue Tau at single residue resolution." *PLoS Biol* 7(2): e34.

Portelius, E., S. F. Hansson, et al. (2008). "Characterization of Tau in cerebrospinal fluid using mass spectrometry." *J Proteome Res* 7(5): 2114-2120.

Smith, P. K., R. I. Krohn, et al. (1985). "Measurement of protein using bicinchoninic acid." *Anal Biochem* 150(1): 76-85.

Stewart, et al., *Solid-Phase Peptide Synthesis*, 2nd Edition, Pierce Chemical Co., Rockford, Ill. (1984)).

---

What is claimed is:

1. A modified peptide that consists of an N-terminal reactive region, a C-terminal reactive region, and a PEG6 linker region, wherein:
   (a) the N-terminal reactive region consists of an amino acid sequence selected from the group of SEQ ID NOs: 7, 8, 9, and 10; and
   (b) the C-terminal reactive region consists of an amino acid sequence selected from the group of SEQ ID NOs: 7, 8, 9 and 10; and
   (c) wherein the linker region consists essentially of a PEG6 linker.

2. The modified peptide of claim 1, wherein the N-terminal and C-terminal reactive regions respectively consists of the amino acid sequences selected from the group consisting of SEQ ID NOs: 7 and 9, SEQ ID NOs: 7 and 8, SEQ ID NOs: 8 and SEQ ID NOs: 8 and 7, SEQ ID NOs: 10 and 9, SEQ ID NOs: 9 and 7, SEQ ID NOs: 9 and 8; and, SEQ ID Nos: 9 and 10, respectively.

3. The modified peptide of claim 2, wherein the N-terminal and C-terminal reactive regions consists essentially of the amino acid sequences set forth in SEQ ID NOs: 7 and 9, respectively.

4. The modified peptide of claim 1, wherein the PEG6 linker has the following structure:

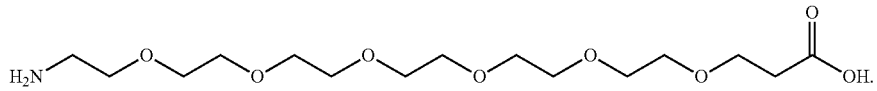 [SMILES: NCCOCCOCCOCCOCCOCCOCCC(=O)O]

5. The modified peptide of claim 1, wherein the linker region is a non-immunoreactive domain.

6. The modified peptide of claim 2 wherein the peptide is SEQ ID: 24.

7. A composition comprising the modified peptide of claim 1 and a carrier.

8. A composition comprising a modified peptide consisting of an N-terminal reactive region, a C-terminal reactive region, and a PEG6 linker region, wherein the N-terminal and C-terminal reactive regions are linked by the PEG6 linker region and wherein said modified peptide is selected from the group consisting of:
  (a) the N-terminal reactive region consists of the amino acid sequence set forth in SEQ ID NO: 7 and the C-terminal reactive region consists of the amino acid sequence set forth in SEQ ID NO: 9;
  (b) the N-terminal region consists of the amino acid sequence set forth in SEQ ID NO: 8 and the C-terminal region consists essentially of the amino acid sequence set forth in SEQ ID NO: 7;
  (c) the N-terminal region consists of the amino acid sequence set forth in SEQ ID NO: 8 and the C-terminal reactive region consists essentially of the amino acid sequence set forth in SEQ ID NO: 9;
  (d) the N-terminal reactive region consists of the amino acid sequence set forth in SEQ ID NO: 10 and the C-terminal reactive region consists of the amino acid sequence set forth in SEQ ID NO: 9;
  (e) the N-terminal region consists of the amino acid sequence set forth in SEQ ID NO: 7 and the C-terminal reactive region consists of the amino acid sequence set forth in SEQ ID NO: 8;
  (f) the N-terminal reactive region consists of the amino acid sequence set forth in SEQ ID NO: 9 and the C-terminal reactive region consists of the amino acid sequence set forth in SEQ ID NO: 7; and
  (g) the N-terminal reactive region consists of the amino acid sequence set forth in SEQ ID NO: 9 and the C-terminal reactive region consists of the amino acid sequence set forth in SEQ ID NO: 8.

9. The modified peptide of claim 8, wherein the N-terminal and C-terminal reactive regions consist of the amino acid sequences set forth in SEQ ID NOs: 7 and 9, respectively.

* * * * *

SEQUENCE LISTING

```
<160> NUMBER OF SEQ ID NOS: 54

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270
```

```
Gly Lys Val Gln Ile Ile Asn Lys Leu Asp Leu Ser Asn Val Gln
            275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 2
<211> LENGTH: 410
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205
```

```
Arg Ser Arg Thr Pro Ser Leu Pro Thr Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
        290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
                340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
        370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 3
<211> LENGTH: 412
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
```

```
                165                 170                 175
Pro Gly Ser Arg Ser Arg Thr Pro Ser Leu Pro Thr Pro Pro Thr Arg
            180                 185                 190

Glu Pro Lys Lys Val Ala Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
            245                 250                 255

Asn Val Gln Ser Lys Cys Gly Ser Lys Asp Asn Ile Lys His Val Pro
        260                 265                 270

Gly Gly Gly Ser Val Gln Ile Val Tyr Lys Pro Val Asp Leu Ser Lys
    275                 280                 285

Val Thr Ser Lys Cys Gly Ser Leu Gly Asn Ile His His Lys Pro Gly
290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
            325                 330                 335

Gly Gly Asn Lys Lys Ile Glu Thr His Lys Leu Thr Phe Arg Glu Asn
        340                 345                 350

Ala Lys Ala Lys Thr Asp His Gly Ala Glu Ile Val Tyr Lys Ser Pro
    355                 360                 365

Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
            405                 410

<210> SEQ ID NO 4
<211> LENGTH: 381
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
            85                  90                  95

Arg Met Val Ser Lys Ser Lys Asp Gly Thr Gly Ser Asp Asp Lys Lys
        100                 105                 110

Ala Lys Gly Ala Asp Gly Lys Thr Lys Ile Ala Thr Pro Arg Gly Ala
    115                 120                 125
```

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
    370                 375                 380

<210> SEQ ID NO 5
<211> LENGTH: 383
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 6
<211> LENGTH: 352
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly

```
            115                 120                 125
Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
                195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
                260                 265                 270

His Val Pro Gly Gly Gly Asn Lys Lys Ile Glu Thr His Lys Leu Thr
                275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
                340                 345                 350

<210> SEQ ID NO 7
<211> LENGTH: 20
<212> TYPE: PRT
<213> ORGANISM: Homo sapiens

<400> SEQUENCE: 7

Lys Ser Gly Asp Arg Ser Gly Tyr Ser Ser Pro Gly Ser Pro Gly Thr
1               5                   10                  15

Pro Gly Ser Arg
            20

<210> SEQ ID NO 8
<211> LENGTH: 16
<212> TYPE: PRT
<213> ORGANISM: Homo sapiens

<400> SEQUENCE: 8

Arg Gly Ala Ala Pro Pro Gly Gln Lys Gly Gln Ala Asn Ala Thr Arg
1               5                   10                  15

<210> SEQ ID NO 9
<211> LENGTH: 16
<212> TYPE: PRT
<213> ORGANISM: Homo sapiens

<400> SEQUENCE: 9

Leu Pro Thr Pro Pro Thr Arg Glu Pro Lys Lys Val Ala Val Val Arg
1               5                   10                  15
```

```
<210> SEQ ID NO 10
<211> LENGTH: 16
<212> TYPE: PRT
<213> ORGANISM: Homo sapiens

<400> SEQUENCE: 10

Lys Thr Pro Pro Ser Ser Gly Glu Pro Pro Lys Ser Gly Asp Arg Ser
1               5                   10                  15

<210> SEQ ID NO 11
<211> LENGTH: 10
<212> TYPE: PRT
<213> ORGANISM: Homo sapiens

<400> SEQUENCE: 11

Ser Gly Asp Arg Ser Gly Tyr Ser Ser Pro
1               5                   10

<210> SEQ ID NO 12
<211> LENGTH: 12
<212> TYPE: PRT
<213> ORGANISM: Homo sapiens

<400> SEQUENCE: 12

Gly Ala Ala Pro Pro Gly Gln Lys Gly Gln Ala Asn
1               5                   10

<210> SEQ ID NO 13
<211> LENGTH: 20
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated Thr

<400> SEQUENCE: 13

Ile Pro Ala Lys Thr Pro Pro Ala Pro Lys Thr Pro Pro Ser Ser Gly
1               5                   10                  15

Glu Pro Pro Lys
            20

<210> SEQ ID NO 14
<211> LENGTH: 20
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Phosphorylated Thr

<400> SEQUENCE: 14

Arg Glu Pro Lys Lys Val Ala Val Val Arg Thr Pro Pro Lys Ser Pro
1               5                   10                  15

Ser Ser Ala Lys
            20

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 15

Ser Gly Asp Arg Ser Gly Tyr Ser Ser Pro
1               5                   10

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (20)..(21)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 16

Lys Ser Gly Asp Arg Ser Gly Tyr Ser Ser Pro Gly Ser Pro Gly Thr
1               5                   10                  15

Pro Gly Ser Arg Leu Pro Thr Pro Pro Thr Arg Glu Pro Lys Lys Val
            20                  25                  30

Ala Val Val Arg
        35

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (16)..(17)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 17

Arg Gly Ala Ala Pro Pro Gly Gln Lys Gly Gln Ala Asn Ala Thr Arg
1               5                   10                  15

Lys Ser Gly Asp Arg Ser Gly Tyr Ser Ser Pro Gly Ser Pro Gly Thr
            20                  25                  30

Pro Gly Ser Arg
        35

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (16)..(17)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 18

Arg Gly Ala Ala Pro Pro Gly Gln Lys Gly Gln Ala Asn Ala Thr Arg
1               5                   10                  15

Leu Pro Thr Pro Pro Thr Arg Glu Pro Lys Lys Val Ala Val Val Arg
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (16)..(17)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 19

Lys Thr Pro Pro Ser Ser Gly Glu Pro Pro Lys Ser Gly Asp Arg Ser
1               5                   10                  15

Leu Pro Thr Pro Pro Thr Arg Glu Pro Lys Lys Val Ala Val Val Arg
            20                  25                  30

<210> SEQ ID NO 20
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (16)..(17)
<223> OTHER INFORMATION: Residues at these positions are separated by a
      PEG6 linker
<220> FEATURE:
<223> OTHER INFORMATION: See specification as filed for detailed
      description of substitutions and preferred embodiments

<400> SEQUENCE: 20

Arg Gly Ala Ala Pro Pro Gly Gln Lys Gly Gln Ala Asn Ala Thr Arg
1               5                   10                  15

Lys Ser Gly Asp Arg Ser Gly Tyr Ser Ser Pro Gly Ser Pro Gly Thr
            20                  25                  30

Pro Gly Ser Arg
        35

<210> SEQ ID NO 21
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Arg Gly Ala Ala Pro Pro Gly Gln Lys Gly Gln Ala Asn Ala Thr Arg
1               5                   10                  15

Gly Gly Ser Gly Gly Ser Lys Ser Gly Asp Arg Ser Gly Tyr Ser Ser
            20                  25                  30

Pro Gly Ser Pro Gly Thr Pro Gly Ser Arg
        35                  40

```
<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (20)..(21)
<223> OTHER INFORMATION: Residues at these positions are separated by a
      PEG6 linker
<220> FEATURE:
<223> OTHER INFORMATION: See specification as filed for detailed
      description of substitutions and preferred embodiments

<400> SEQUENCE: 22

Lys Ser Gly Asp Arg Ser Gly Tyr Ser Ser Pro Gly Ser Pro Gly Thr
1               5                   10                  15

Pro Gly Ser Arg Arg Gly Ala Ala Pro Pro Gly Gln Lys Gly Gln Ala
            20                  25                  30

Asn Ala Thr Arg
        35

<210> SEQ ID NO 23
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Lys Ser Gly Asp Arg Ser Gly Tyr Ser Ser Pro Gly Ser Pro Gly Thr
1               5                   10                  15

Pro Gly Ser Arg Gly Gly Ser Gly Gly Ser Arg Gly Ala Ala Pro Pro
            20                  25                  30

Gly Gln Lys Gly Gln Ala Asn Ala Thr Arg
        35                  40

<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (20)..(21)
<223> OTHER INFORMATION: Residues at these positions are separated by a
      PEG6 linker
<220> FEATURE:
<223> OTHER INFORMATION: See specification as filed for detailed
      description of substitutions and preferred embodiments

<400> SEQUENCE: 24

Lys Ser Gly Asp Arg Ser Gly Tyr Ser Ser Pro Gly Ser Pro Gly Thr
1               5                   10                  15

Pro Gly Ser Arg Leu Pro Thr Pro Pro Thr Arg Glu Pro Lys Lys Val
            20                  25                  30

Ala Val Val Arg
        35

<210> SEQ ID NO 25
```

```
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Lys Ser Gly Asp Arg Ser Gly Tyr Ser Ser Pro Gly Ser Pro Gly Thr
1               5                   10                  15

Pro Gly Ser Arg Gly Gly Ser Gly Gly Ser Leu Pro Thr Pro Pro Thr
            20                  25                  30

Arg Glu Pro Lys Lys Val Ala Val Val Arg
        35                  40

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (16)..(17)
<223> OTHER INFORMATION: Residues at these positions are separated by a
      PEG6 linker
<220> FEATURE:
<223> OTHER INFORMATION: See specification as filed for detailed
      description of substitutions and preferred embodiments

<400> SEQUENCE: 26

Leu Pro Thr Pro Pro Thr Arg Glu Pro Lys Lys Val Ala Val Val Arg
1               5                   10                  15

Lys Ser Gly Asp Arg Ser Gly Tyr Ser Ser Pro Gly Ser Pro Gly Thr
            20                  25                  30

Pro Gly Ser Arg
        35

<210> SEQ ID NO 27
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Pro Thr Pro Pro Thr Arg Glu Pro Lys Lys Val Ala Val Val Arg
1               5                   10                  15

Gly Gly Ser Gly Gly Ser Lys Ser Gly Asp Arg Ser Gly Tyr Ser Ser
            20                  25                  30

Pro Gly Ser Pro Gly Thr Pro Gly Ser Arg
        35                  40

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Arg Gly Ala Ala Pro Pro Gly Gln Lys Gly Gln Ala Asn Ala Thr Arg
1               5                   10                  15
```

```
Gly Gly Ser Gly Gly Ser Leu Pro Thr Pro Pro Thr Arg Glu Pro Lys
            20                  25                  30

Lys Val Ala Val Val Arg
        35

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (16)..(17)
<223> OTHER INFORMATION: Residues at these positions are separated by a
      PEG6 linker
<220> FEATURE:
<223> OTHER INFORMATION: See specification as filed for detailed
      description of substitutions and preferred embodiments

<400> SEQUENCE: 29

Leu Pro Thr Pro Pro Thr Arg Glu Pro Lys Lys Val Ala Val Val Arg
1               5                   10                  15

Arg Gly Ala Ala Pro Pro Gly Gln Lys Gly Gln Ala Asn Ala Thr Arg
            20                  25                  30

<210> SEQ ID NO 30
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Leu Pro Thr Pro Pro Thr Arg Glu Pro Lys Lys Val Ala Val Val Arg
1               5                   10                  15

Gly Gly Ser Gly Gly Ser Arg Gly Ala Ala Pro Pro Gly Gln Lys Gly
            20                  25                  30

Gln Ala Asn Ala Thr Arg
        35

<210> SEQ ID NO 31
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (20)..(21)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 31

Lys Ser Gly Asp Arg Ser Gly Tyr Ser Ser Pro Gly Ser Pro Gly Thr
1               5                   10                  15

Pro Gly Ser Arg Arg Gly Ala Ala Pro Pro Gly Gln Lys Gly Gln Ala
            20                  25                  30

Asn Ala Thr Arg
        35
```

```
<210> SEQ ID NO 32
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (16)..(17)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 32

Leu Pro Thr Pro Pro Thr Arg Glu Pro Lys Lys Val Ala Val Val Arg
1               5                   10                  15

Lys Ser Gly Asp Arg Ser Gly Tyr Ser Ser Pro Gly Ser Pro Gly Thr
                20                  25                  30

Pro Gly Ser Arg
            35

<210> SEQ ID NO 33
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (16)..(17)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 33

Arg Gly Ala Ala Pro Pro Gly Gln Lys Gly Gln Ala Asn Ala Thr Arg
1               5                   10                  15

Leu Pro Thr Pro Pro Thr Arg Glu Pro Lys Lys Val Ala Val Val Arg
                20                  25                  30

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (16)..(17)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 34

Leu Pro Thr Pro Pro Thr Arg Glu Pro Lys Lys Val Ala Val Val Arg
1               5                   10                  15

Arg Gly Ala Ala Pro Pro Gly Gln Lys Gly Gln Ala Asn Ala Thr Arg
                20                  25                  30
```

```
<210> SEQ ID NO 35
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (12)..(13)
<223> OTHER INFORMATION: Residues at these positions are separated by an
      undefined amino acid or non-amino acid type linker
<220> FEATURE:
<221> NAME/KEY: MOD_RES
<222> LOCATION: (23)..(23)
<223> OTHER INFORMATION: Phosphorylated Thr
<220> FEATURE:
<223> OTHER INFORMATION: See specification as filed for detailed
      description of substitutions and preferred embodiments

<400> SEQUENCE: 35

Gly Ala Ala Pro Pro Gly Gln Lys Gly Gln Ala Asn Arg Glu Pro Lys
1               5                   10                  15

Lys Val Ala Val Val Arg Thr Pro Pro Lys Ser Pro Ser Ser Ala Lys
            20                  25                  30

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (12)..(13)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 36

Gly Ala Ala Pro Pro Gly Gln Lys Gly Gln Ala Asn Ser Gly Asp Arg
1               5                   10                  15

Ser Gly Tyr Ser Ser Pro
            20

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Phosphorylated Thr
<220> FEATURE:
<221> NAME/KEY: misc_feature
<222> LOCATION: (20)..(21)
<223> OTHER INFORMATION: Residues at these positions are separated by an
      undefined amino acid or non-amino acid type linker
<220> FEATURE:
<223> OTHER INFORMATION: See specification as filed for detailed
      description of substitutions and preferred embodiments

<400> SEQUENCE: 37

Ile Pro Ala Lys Thr Pro Pro Ala Pro Lys Thr Pro Pro Ser Ser Gly
1               5                   10                  15
```

```
Glu Pro Pro Lys Ser Gly Asp Arg Ser Gly Tyr Ser Ser Pro
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (10)..(11)
<223> OTHER INFORMATION: Residues at these positions are separated by an
      undefined amino acid or non-amino acid type linker
<220> FEATURE:
<221> NAME/KEY: MOD_RES
<222> LOCATION: (21)..(21)
<223> OTHER INFORMATION: Phosphorylated Thr
<220> FEATURE:
<223> OTHER INFORMATION: See specification as filed for detailed
      description of substitutions and preferred embodiments

<400> SEQUENCE: 38

Ser Gly Asp Arg Ser Gly Tyr Ser Ser Pro Arg Glu Pro Lys Lys Val
1               5                   10                  15

Ala Val Val Arg Thr Pro Pro Lys Ser Pro Ser Ser Ala Lys
            20                  25                  30

<210> SEQ ID NO 39

<400> SEQUENCE: 39

000

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Ser Gly Gly Ser
1               5

<210> SEQ ID NO 41

<400> SEQUENCE: 41

000

<210> SEQ ID NO 42
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Arg Met Val Ser Lys Ser Lys Asp Gly Thr Gly Ser Asp Asp Lys Lys
1               5                   10                  15

Ala Lys Gly Ala Asp Gly Lys Thr Lys Ile Ala Thr Pro Arg Gly Ala
            20                  25                  30

Ala Pro Pro Gly Gln Lys Gly Gln Ala Asn Ala Thr Arg Ile Pro Ala
```

-continued

```
               35                  40                  45
Lys Thr Pro Pro Ala Pro Lys Thr Pro Pro Ser Ser
    50                  55                  60

<210> SEQ ID NO 43
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys His Val Thr Gln Ala Arg Met Val Ser Ser Lys Asp Gly Thr
1               5                   10                  15

Gly Ser Asp Asp Lys
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Gly Ser Asp Asp Lys Lys Ala Lys Gly Ala Asp Gly Lys Thr Lys
1               5                   10                  15

Ile Ala Thr Pro Arg
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Ile Ala Thr Pro Arg Gly Ala Ala Pro Pro Gly Gln Lys Gly Gln
1               5                   10                  15

Ala Asn Ala Thr Arg
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Ala Asn Ala Thr Arg Ile Pro Ala Lys Thr Pro Pro Ala Pro Lys
1               5                   10                  15

Thr Pro Pro Ser Ser
            20

<210> SEQ ID NO 47
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 47

Cys Arg Gly Ala Ala Pro Pro Gly Gln Lys Gly Gln Ala Asn Ala Thr
1               5                   10                  15

Arg

<210> SEQ ID NO 48
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Glu Pro Pro Lys Ser Gly Asp Arg Ser Gly Tyr Ser Ser Pro Gly
1               5                   10                  15

Ser Pro Gly Thr Pro Gly Ser Arg Ser Arg Thr Pro Ser Leu Pro Thr
            20                  25                  30

Pro Pro Thr Arg Glu Pro Lys Lys Val Ala Val Val Arg Thr Pro Pro
        35                  40                  45

Lys Ser Pro Ser Ser Ala Lys Ser Arg Leu Gln Thr
    50                  55                  60

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Thr Pro Pro Ser Ser Gly Glu Pro Pro Lys Ser Gly Asp Arg Ser
1               5                   10                  15

Gly Tyr Ser Ser Pro
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Gly Tyr Ser Ser Pro Gly Ser Pro Gly Thr Pro Gly Ser Arg Ser
1               5                   10                  15

Arg Thr Pro Ser Leu
            20

<210> SEQ ID NO 51
<211> LENGTH: 21
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 51

Lys Arg Thr Pro Ser Leu Pro Thr Pro Pro Thr Arg Glu Pro Lys Lys
1               5                   10                  15

Val Ala Val Val Arg
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Val Ala Val Val Arg Thr Pro Pro Lys Ser Pro Ser Ser Ala Lys
1               5                   10                  15

Ser Arg Leu Gln Thr
            20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Lys Ser Gly Asp Arg Ser Gly Tyr Ser Ser Pro Gly Ser Pro Gly
1               5                   10                  15

Thr Pro Gly Ser Arg
            20

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Leu Pro Thr Pro Pro Thr Arg Glu Pro Lys Lys Val Ala Val Val
1               5                   10                  15

Arg
```